(12) United States Patent
Gillman et al.

(10) Patent No.: US 9,211,128 B2
(45) Date of Patent: Dec. 15, 2015

(54) DEVICES AND METHODS FOR HIP REPLACEMENT

(71) Applicants: Michael Gillman, Laguna Beach, CA (US); Benjamin A. Gillman, Laguna Beach, CA (US)

(72) Inventors: Michael Gillman, Laguna Beach, CA (US); Benjamin A. Gillman, Laguna Beach, CA (US)

(73) Assignee: BULLSEYE Hip Replacement, LLC, Las Vegas, NV (US)

( * ) Notice: Subject to any disclaimer, the term of this patent is extended or adjusted under 35 U.S.C. 154(b) by 0 days.

(21) Appl. No.: 14/255,761

(22) Filed: Apr. 17, 2014

(65) Prior Publication Data

US 2015/0297248 A1   Oct. 22, 2015

(51) Int. Cl.
*A61F 5/00* (2006.01)
*A61B 17/17* (2006.01)

(52) U.S. Cl.
CPC ......... *A61B 17/1746* (2013.01); *A61B 17/1703* (2013.01)

(58) Field of Classification Search
CPC ............. A61B 17/155; A61B 17/1664; A61B 17/1666
USPC ............. 606/54–59, 79–81, 86 R, 87–91, 96; 623/22.11–22.46
See application file for complete search history.

(56) References Cited

U.S. PATENT DOCUMENTS

| | | |
|---|---|---|
| 5,474,560 A | 12/1995 | Rohr, Jr. |
| 8,617,170 B2 | 12/2013 | Ashby et al. |
| 8,617,171 B2 | 12/2013 | Park et al. |
| 8,777,875 B2 | 7/2014 | Park |
| 2005/0148843 A1 | 7/2005 | Roose |
| 2007/0219562 A1 | 9/2007 | Slone et al. |
| 2010/0016860 A1 | 1/2010 | McCardel |
| 2010/0082035 A1* | 4/2010 | Keefer ............................ 606/91 |
| 2010/0274253 A1* | 10/2010 | Ure ................................. 606/91 |
| 2011/0093086 A1 | 4/2011 | Witt et al. |
| 2011/0190775 A1 | 8/2011 | Ure |
| 2011/0214279 A1 | 9/2011 | Park et al. |
| 2012/0041445 A1* | 2/2012 | Roose et al. ..................... 606/96 |
| 2012/0296339 A1 | 11/2012 | Iannotti et al. |
| 2013/0123789 A1 | 5/2013 | Park |
| 2013/0184764 A1 | 7/2013 | Stone et al. |
| 2013/0190768 A1 | 7/2013 | Aram et al. |
| 2013/0317510 A1 | 11/2013 | Couture et al. |
| 2014/0025348 A1 | 1/2014 | Abiven |
| 2014/0128875 A1 | 5/2014 | Park et al. |
| 2014/0128876 A1 | 5/2014 | Aram et al. |
| 2014/0142580 A1 | 5/2014 | Aram et al. |

FOREIGN PATENT DOCUMENTS

| | | |
|---|---|---|
| EP | 2 168 507 A2 | 3/2010 |
| WO | 2009/098491 A1 | 8/2009 |

(Continued)

*Primary Examiner* — Matthew Lawson
(74) *Attorney, Agent, or Firm* — Seed IP Law Group PLLC

(57) ABSTRACT

Devices and methods for use in hip replacement surgery can incorporate computer models of a patient's acetabulum and surrounding bone structure, a first patient-specific jig designed from the computer model and configured to correspond to a final installation position and orientation of a prosthetic hip implant, a second patient-specific jig, also designed from the computer model, configured to refine the procedure, if necessary, following use of the first patient-specific jig, and/or a third patient specific jig, designed from the computer model, configured to refine the procedure, if necessary, following use of the first and second patient-specific jigs, allowing the surgeon to properly position and orient the hip prosthesis. Also shown and described are novel devices for implanting an acetabular cup.

18 Claims, 21 Drawing Sheets

FOREIGN PATENT DOCUMENTS

| | | |
|---|---|---|
| WO | 2010/124164 A1 | 10/2010 |
| WO | 2011/060536 A1 | 5/2011 |
| WO | 2011/110374 A1 | 9/2011 |
| WO | 2010/021846 A2 | 2/2012 |
| WO | 2012/021849 A2 | 2/2012 |
| WO | 2013/188960 A1 | 12/2013 |

* cited by examiner

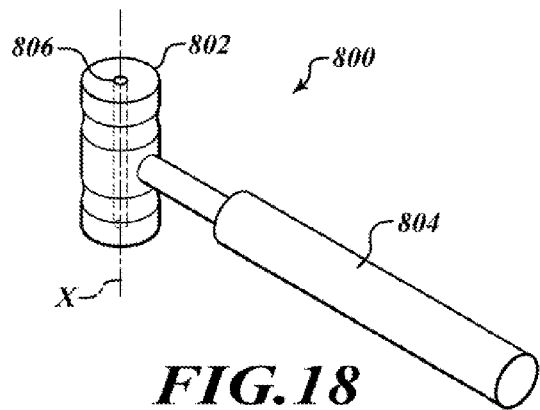
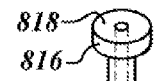
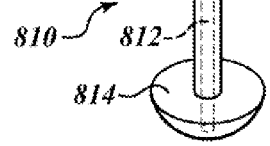
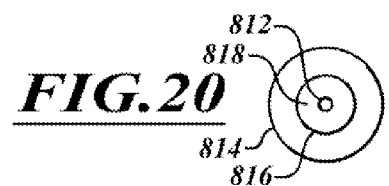
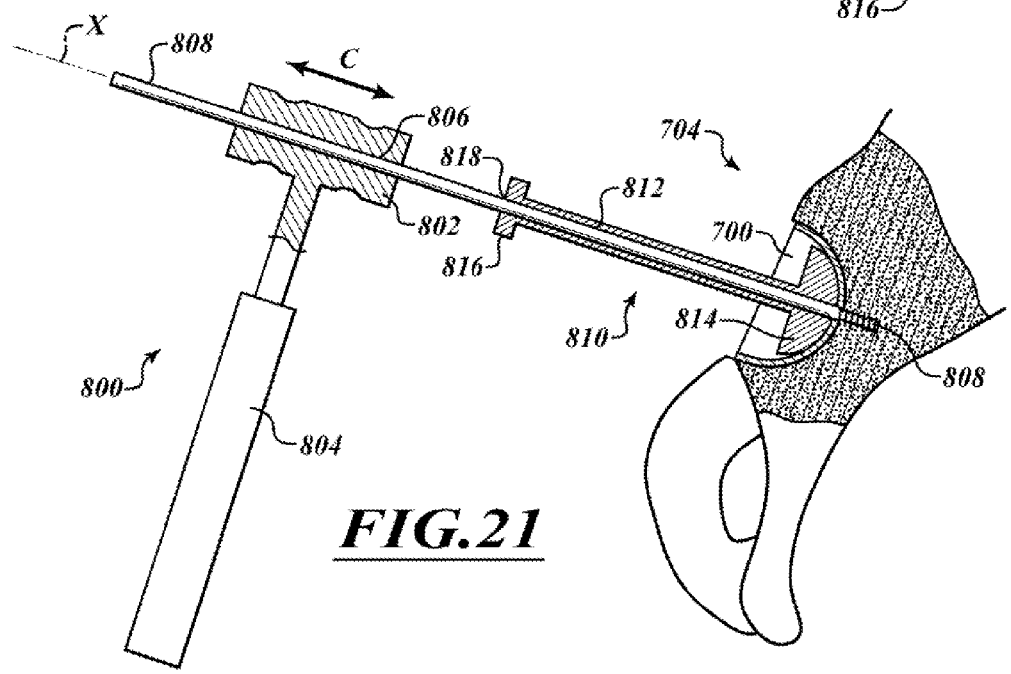
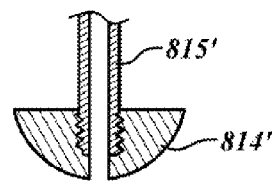

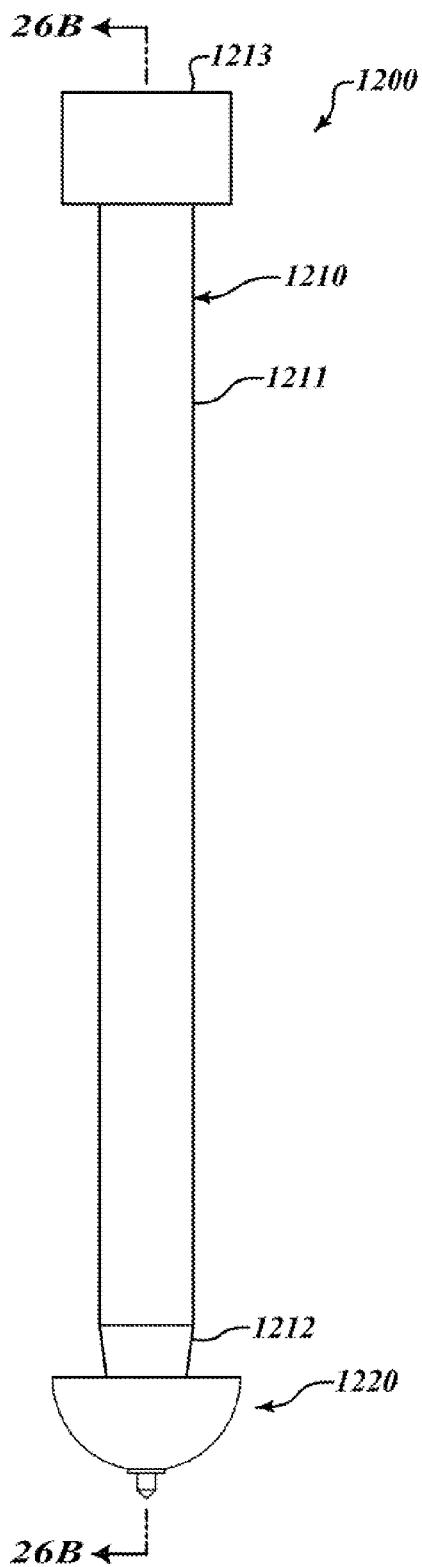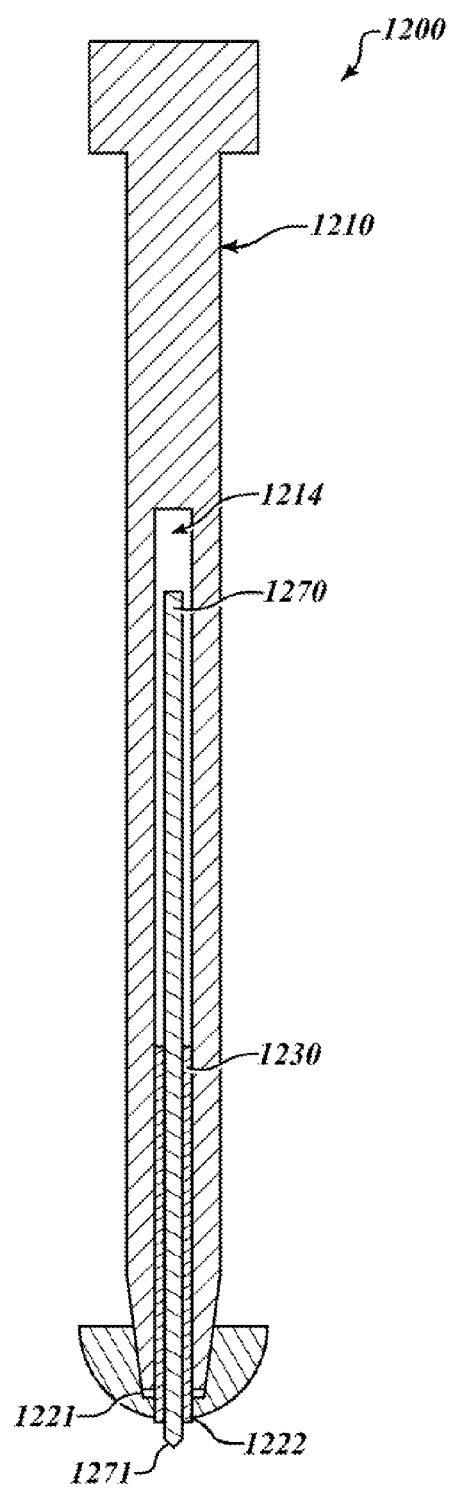
*FIG.26A*  *FIG.26B*

DEVICES AND METHODS FOR HIP REPLACEMENT

BACKGROUND

1. Technical Field

The present disclosure relates to devices and methods for the replacement of joints, and more particularly, to patient-specific hip replacement devices, including methods of manufacturing and using such devices for achieving accurate hip replacement based on computer generated imaging of a patient.

2. Background of the Invention

One known method of treating hip and other joints with arthritis and other medical conditions is to replace surfaces of articulating joints with prosthetic devices through surgical procedures. It is critical that such prosthetic devices are accurately designed and manufactured, and are installed correctly in order to relieve pain and provide an effective treatment method for such ailments. An orthopedic surgeon performing such joint replacement on a patient seeks to ensure, through surgery, adequate placement of the prosthetic and proper reconstruction of the joint being replaced. Prosthetic components used to replace a joint may be placed optimally by templates and jigs according to the unique anatomy of a patient before surgery occurs. A particular patient's bone structure symmetry is one important consideration that a surgeon must consider when performing joint replacement surgery. Additionally, malposition of joint replacement prosthetics can result in premature wear of the bearing surfaces, which may require additional surgeries to correct.

In the case of a hip, the condition of the patient's joint may require a partial or total replacement. A partial hip replacement involves replacing the femoral head (the ball) of the damaged hip joint; however, the acetabulum (the socket) is not replaced in a partial hip replacement surgery. A total hip replacement includes replacing both the femoral head and the acetabulum with prosthetic devices. The femoral head is replaced with a femoral prosthetic that typically includes a head portion and a stem. The stem extends into the femur of the patient and is utilized to secure the femoral device to the femur, with the head portion protruding out from the femur. The acetabulum is then resurfaced and replaced with a cup-shaped acetabular device. The cup-shaped acetabular device provides a bearing surface for the head portion of the femoral prosthetic to allow a desirable amount of range of motion via the joint upon total hip replacement.

To replace the acetabulum effectively, a surgeon will typically enlarge the acetabulum with a reamer machine and reamer head to create a resurfaced cavity to receive a prosthetic acetabular cup, which may or may not be secured by cement or bone screws. One particular issue of concern during the reaming portion of the surgery is that the cutting portion of the reamer is hemispherical while the prosthetic acetabular cup is typically sub-hemispherical. If the acetabulum is reamed too deeply, the prosthetic acetabular cup will be positioned too deep within the reamed cavity. If the acetabulum is reamed too shallowly, the prosthetic acetabular cup will not be positioned deep enough. If the acetabulum is reamed at an improper angle, the prosthetic acetabular cup will not be installed properly. These imperfections can cause malalignment of the prosthetic hip joint. Moreover even if the acetabular bone is properly reamed, it is quite difficult with standard techniques to place the acetabular prosthetic cup. Recent studies, reflect a 50% rate of error in placement of the acetabular cup from an acceptably optimal range of positions when standard techniques are utilized. Thus, accurate reaming of the acetabulum and accurate positioning of the prosthetic acetabular cup are critical.

With the assistance of computer generated data derived from CT, MRI, or other scans, such as X-rays, surgeons can more effectively determine proper alignment and positioning of the prosthetic acetabular cup in a patient through 3D modeling and rendering. While some surgeons use lasers or peripheral guide pins during surgery in an attempt to properly place the prosthetic acetabular cup; however, accuracy and simplicity of existing devices and methods remain limited due to a variety of factors.

BRIEF SUMMARY

The present disclosure pertains to patient-specific hip replacement devices and methods of designing and manufacturing such devices for achieving accurate acetabular component placement during hip replacement surgery based on computer generated imaging of a particular patient. When an orthopedic surgeon recommends total hip replacement surgery for a particular patient, a variety of images may be obtained utilizing CT, MRI, and other scans, such as x-rays, to generate 3D modeling of the patient's bone structure, particularly the femur, the pelvic bone, and the coxal (hip) bone. From such 3D models, the surgeon may determine the specific, final location and orientation of an acetabular cup to be secured to the patient's acetabulum during surgery. Once the final location and orientation of the acetabular cup is determined, the surgeon (utilizing 3D images) may create a first patient-specific jig and a second—and in some cases a third—patient-specific jig to be inserted into the patient's acetabulum during the surgery to ultimately achieve accurate positioning of the prosthetics to be installed in the patient.

The first patient-specific jig may be designed and manufactured based on a first patient-specific acetabulum male portion, while the second patient-specific jig may be designed and manufactured based on a second patient-specific acetabulum male portion. The first and second patient-specific acetabulum male portions can be developed as either physical components via a prototyping machine or visual representations in a 3D modeling software program based upon the 3D images of the patient. The male portion may or may not fully contact the patient's native acetabulum.

The first patient-specific jig can be a hemispherical shaped device or a sub-hemispherical shaped device, and can be comprised of composite material or other materials. The first patient-specific jig may include at least three alignment members for attachment to specific portions of the jig based on the specific bone structure of the patient's coxal bone. The at least three alignment members may assist with proper alignment of the first patient-specific jig in the patient's acetabulum during surgery. The three alignment members may include first, second, and third alignment members that are positioned at specific outer portions of the first patient-specific jig.

In some embodiments, the first, second, and third alignment members are designed and adapted to be hooked on or engaged with (or otherwise positioned at) particular portions of the coxal bone adjacent to the acetabulum to stabilize and properly orient the first patient-specific jig into the acetabulum during surgery. The first alignment member may be positioned on the first patient-specific jig to engage a particular portion of the medial rim of the acetabulum of the coxal bone. The second alignment member may be positioned on the first patient-specific jig to engage a particular portion of the greater sciatic notch of the coxal bone. The third alignment member may be positioned on the first patient-specific jig to engage a particular portion of the obturator foramen of the coxal bone. These alignment members may contact any three areas of bone peripheral to the acetabulum. Thus, the first patient-specific jig includes three reference points/members, specific to the patient's acetabulum of the coxal bone, to properly align the first patient-specific jig in the acetabulum during surgery and provide for proper orientation of the reaming machine when resurfacing the acetabulum.

The three alignment members may each comprise a pair of hooks or other devices that provide sufficient engagement with the particular portions of the coxal bone, as determined by the surgeon during preoperation. A person having ordinary skill in the art when reviewing this disclosure will understand that the three alignment members may be secured or removably attached or abutted to the first patient-specific jig by any currently or later known suitable means or attachment methods. The three alignment members may pivot, swivel or otherwise move relative to the first patient-specific jig, or they may be relatively immovable or inflexible to provide sufficient force against respective portions of the coxal bone to ensure proper orientation of the first patient-specific jig.

An aperture may be provided radially into or through the first patient-specific jig. The aperture is adapted to receive a guide pin or post extension through the aperture during surgery. The guide pin or extension is placed into the aperture and is removably secured to the coxal bone of the patient in a particular orientation and at a particular depth, as determined by the surgeon during preoperation. The first patient-specific jig is then removed while the guide post remains positioned in the coxal bone at the desired angle and position. The guide post may then serve as a guide for the reaming machine to accurately ream (resurface) the acetabulum to a predetermined depth and orientation for receiving the acetabular cup. The guide post and the reamer may have the same or similar central axes, as with conventional reaming machines and processes. In some embodiments the guide post may be removed prior to reaming and a surgeon at his discretion may use the guide post sinus tract as a guide to reaming without the guide post at a desired angle and to a desired depth.

As discussed above, it is critical to ream the acetabulum accurately and as determined during preoperation. Accordingly, the second patient-specific jig may be provided to assist in determining accurate reaming and proper alignment of the acetabular cup before the cup is implanted into the patient's acetabulum. As indicated below, a third patient-specific jig may also be used to progressively prepare the acetabulum to properly receive the prosthetic acetabular cup.

The second patient-specific jig may be designed and manufactured based on the second patient-specific male portion, but it may also be based on the first patient-specific male portion. The second patient-specific jig may include at least three alignment members, which may be based on the same or similar positions as the first, second, and third alignment members of the first patient-specific jig, or the positions may be different depending upon the patient's anatomy. The second patient-specific jig may also include an aperture having the same or similar position and orientation as the aperture in the first patient-specific jig, or it may be different. The second patient-specific jig may also have an axial length that is greater than a corresponding axial length of the first patient-specific jig due to the fact that the second patient-specific jig is utilized after some or all of the reaming of the acetabulum has occurred.

After the surgeon has removed the first patient-specific jig and reamed the acetabulum to a predetermined depth and orientation, the reamer device is removed from the acetabulum and the guide post may remain attached to the coxal bone or, in some instances, may be removed. The surgeon may then position the second patient-specific jig into the reamed acetabulum without a pin or, alternatively, onto the original guide pin or post extension, or alternatively over a different pin or post extension used to align the second patient-specific jig. Using the particular shape and size of the second patient-specific jig and, where applicable, the alignment of the aperture through the jig, the surgeon may then rotate and position the second patient-specific jig in the reamed acetabulum to determine whether additional reaming is required in one or more quadrants, or whether the acetabulum has been reamed accurately to receive the prosthetic acetabular cup. In furtherance of such determination, the surgeon may also utilize the alignment members attached to the second patient-specific jig, if they were designed and manufactured for attachment to the jig; it may be that the aperture and the shape of the second patient-specific jig is sufficient for purposes of accurate alignment of the prosthetic acetabular cup.

In some instances, if adequate remaining in any direction has not been accomplished and confirmed with only one or two jigs, there may be a need for additional reaming after which a third jig may be used. The third patient specific jig may be similar or different in regards to alignment members and guide post aperture orientation as the first and/or second patient specific jigs.

Once accurate reaming is accomplished through utilizing some or all of the above described devices and methods, the surgeon may then implant or secure the acetabular prosthetic cup to the reamed acetabulum in a traditional manner, such as with or without screws and with or without cement and with or without use of a guide pin or post extension.

The predetermined orientation of the apertures and the alignment members of both the first and second (and, as applicable, third) patient-specific jigs may provide the surgeon with a quick, accurate means to properly resurface the acetabulum without the use of additional devices and machines. This is possible because the positions of the alignment members of the first, second and third patient-specific jigs are based upon the patient's bone structure, thereby providing three reference points to accurately utilize the first jig, the guide post, the reamer, and the second and third jigs, as planned during preoperation based upon the 3D modeling images of the patient, a combination of two-dimensional radiographic images of the patient, or a combination of three-dimensional and two-dimensional images of a patient.

BRIEF DESCRIPTION OF THE SEVERAL
VIEWS OF THE DRAWINGS

FIGS. 1-4 are flow diagrams illustrating steps for pre-operative imaging and planning for a joint replacement procedure, according to an aspect of the present invention.

FIG. 4A schematically illustrates a system for carrying out the steps of FIGS. 1-4.

FIG. 18 is an isometric view of an impactor tool used to install a prosthetic implant in a reamed acetabulum according to one aspect of the present disclosure.

FIG. 19 is an isometric view of a cannulated acetabular impactor according to an embodiment of the present invention.

FIG. 20 is an end view of the cannulated acetabular impactor of FIG. 19.

FIG. 21 is a partial cross-sectional view of a prosthetic implant in a reamed acetabulum that is being installed with the impactor tool of FIG. 18 and the cannulated acetabular impactor of FIG. 19, according to one aspect of the present disclosure.

FIG. 22 is a cross-sectional view of a portion of another cannulated acetabular impactor according to an alternate embodiment of the invention.

FIG. 26A is a side elevation view of a cannulated impactor.

FIG. 26B is a cross-sectional view of cannulated impactor of FIG. 26A.

DETAILED DESCRIPTION

Figure 1:
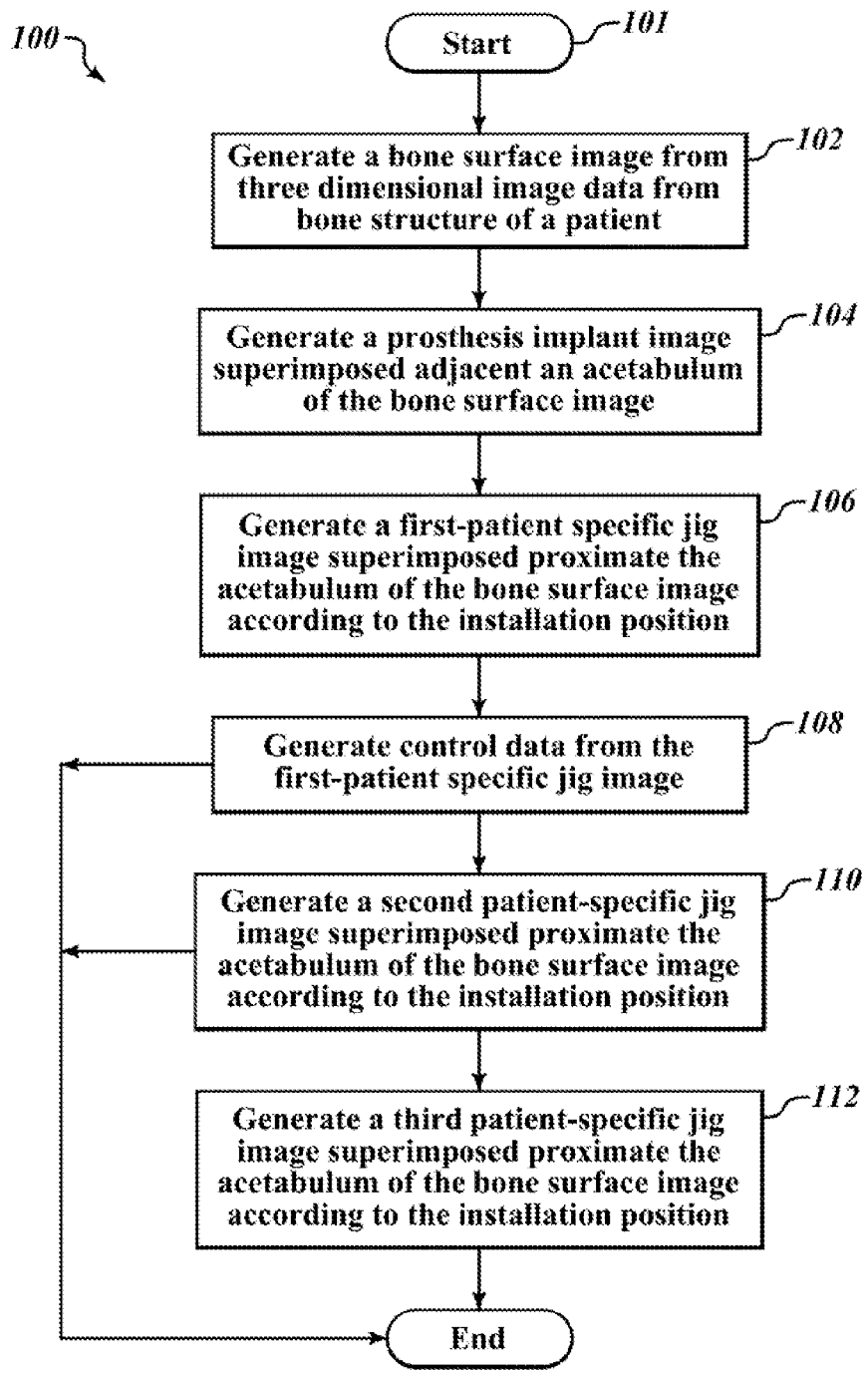

As mentioned above, the methods and systems of the present invention are based at least in part on pre-operating (pre-operative) imaging and at least in part on orthopedic surgical procedures based upon the pre-operative methods and systems. As is understood in the art, pre-operative imaging has a number of different purposes and generally is performed in order to subsequently guide the surgeon during the surgical procedure, allow for patient-specific tools and/or implants to be formed, etc. The present disclosure is part of a system for designing and constructing one or more patient-specific jigs for use in an orthopedic surgical procedure in which an acetabular component is prepared, orientated and implanted. The referenced systems and methods are now described more fully with reference to the accompanying drawings, in which one or more illustrated embodiments and/or arrangements of the systems and methods are shown. Aspects of the present systems and methods can take the form of an entirely hardware embodiment, an entirely software embodiment (including firmware, resident software, microcode, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Throughout this disclosure, the term "prosthetic implant" and "acetabular component" refer to cup-shaped implants that are installed into patients during hip replacement surgery.

FIGS. 1-4 are flow diagrams illustrating methods pertaining to pre-operative imaging and planning according to aspects of the present invention. FIG. 4A shows a system for carrying out the methods of the present disclosure, such as those described with reference to FIGS. 1-4. As a preliminary matter, FIG. 4A is a simplified system 410 of devices that may be used to carry out the methods of the present disclosure. The system 410 comprises a computing system 412 coupled to an imaging system 414 that captures and transmits patient image data to the computing system 412. The computing system 412 processes such data and transmits the data to the display device 416 for display of images and other data. An input device 418 receives input from a computer or an operator (such as a surgeon) and transmits inputted information to the computing system 412 for processing. Such systems are well known in the art and will not be described in greater detail. The imaging system 412 may include a bone imaging machine for forming three-dimensional image data from bone structure of a patient. The computing system 412 may include a patient-specific device generator for processing and generating images, and a patient-specific device converter for generating design control data. A manufacturing machine 420 receives the control data from the computing system 412 for making patient-specific various jigs.

In FIG. 1, a method 100 according to an embodiment starts at 101. At 102, a bone imaging machine generates a bone surface image from three-dimensional image data from bone structure of a patient. At 104, a patient-specific device generator generates a prosthesis implant image superimposed in an acetabulum of the bone surface image. The implant in the image is positioned in its final, implanted position and orientation, regardless of the state of the patient's bone. The jigs created from the present invention will be designed to modify the bone such that the implant will be properly positioned at the end of the procedure.

At 106, the patient-specific device generator generates a first-patient specific jig image superimposed proximate the acetabulum of the bone surface image according to the installation position. At 108, a patient-specific device converter generates control data from the first patient-specific jig image and ends or moves to 110. At 110, the patient-specific device generator generates a second patient-specific jig image superimposed in the acetabulum of the bone surface image and ends or moves to 112. At step 112, the patient-specific device generator generates a third patient-specific jig image superimposed in the acetabulum of the bone surface image and ends.

Figure 2:
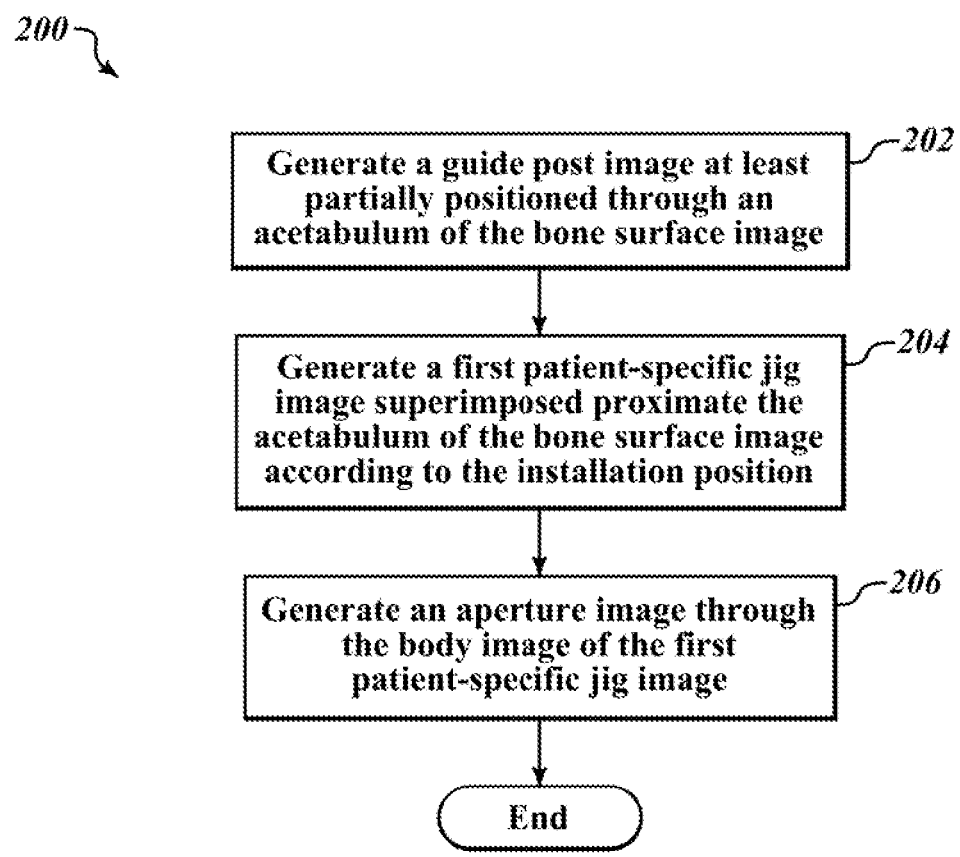

FIG. 2 shows a method 200 according to an aspect of the present disclosure. At 202, a patient-specific device generator generates a guide post image at least partially positioned through an acetabulum of the bone surface image. At 204, the patient-specific device generator generates a first patient-specific jig image superimposed in the acetabulum of the bone surface image according to the installation position. At 206, the patient-specific device generator generates an aperture image through the body image of the second patient-specific jig image and ends.

Figure 3:
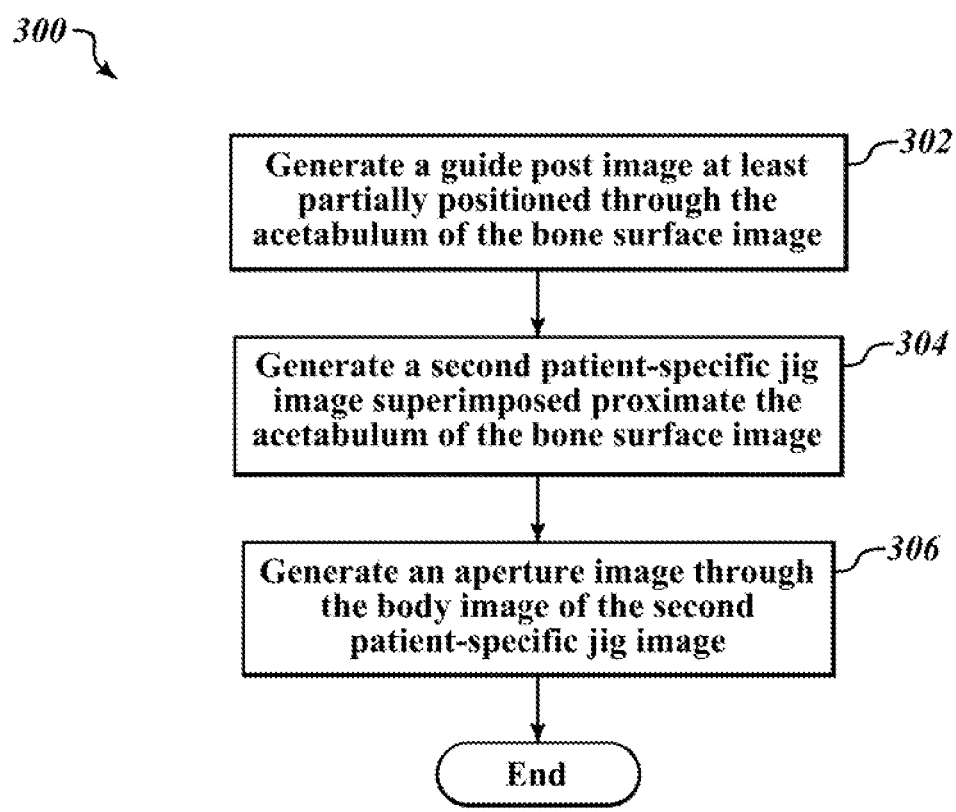

FIG. 3 shows a method 300 according to an aspect of the present disclosure. At 302, a patient-specific device generator generates a guide post image at least partially positioned through an acetabulum of the bone surface image. At 304, the patient-specific device generator generates a second patient-specific jig image superimposed in the acetabulum of the bone surface image according to the installation position. At 306, the patient-specific device generator generates an aperture image through the body image of the first patient-specific jig image and ends.

Figure 4:
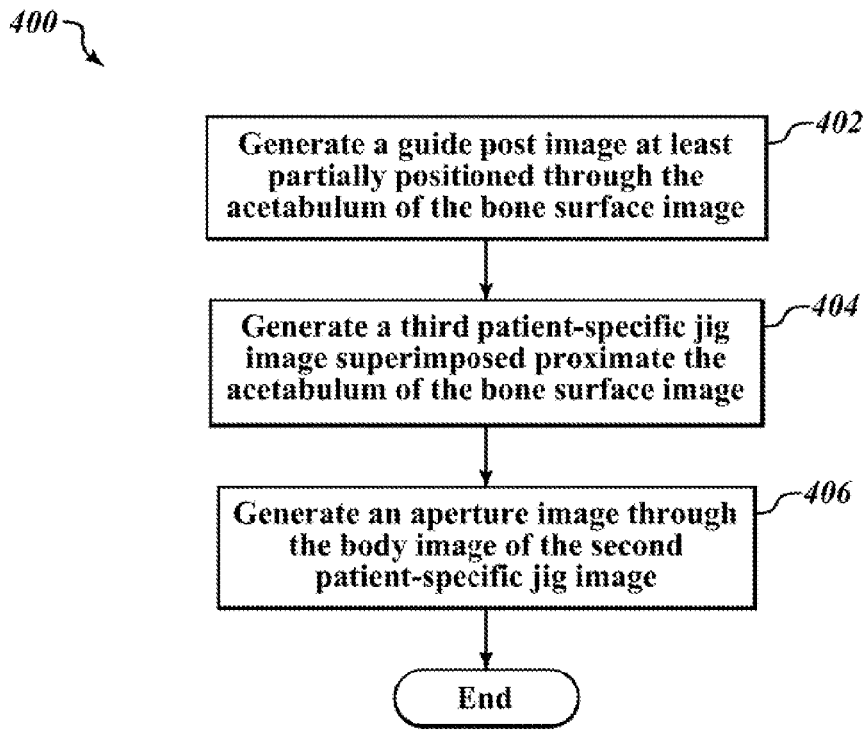

FIG. 4 shows a method 400 according to an aspect of the present disclosure. At 402, a patient-specific device generator generates a guide post image at least partially positioned through an acetabulum of the bone surface image. At 404, the patient-specific device generator generates a third patient-specific jig image superimposed in the acetabulum of the bone surface image according to the installation position. At 306, the patient-specific device generator generates an aperture image through the body image of the third patient-specific jig image and ends.

As discussed above, FIG. 4A shows a system 410 for carrying out the methods of FIGS. 1-4 according to some aspects of the present disclosure. The computing system 412 may include instructions in the form of computer software for automatically generating images of prosthesis implants in final installation positions on the bone structure images and for automatically generating various guide post images and jig images designed for use during surgery on the particular patient. In some aspects, it may be necessary for the surgeon during preoperative planning to input information into the input device 418 for creating or altering guide post and jig images for a particular patient based on the surgeon's understanding of the particular bone structure of the patient as displayed on the display device 416.

Figure 5:
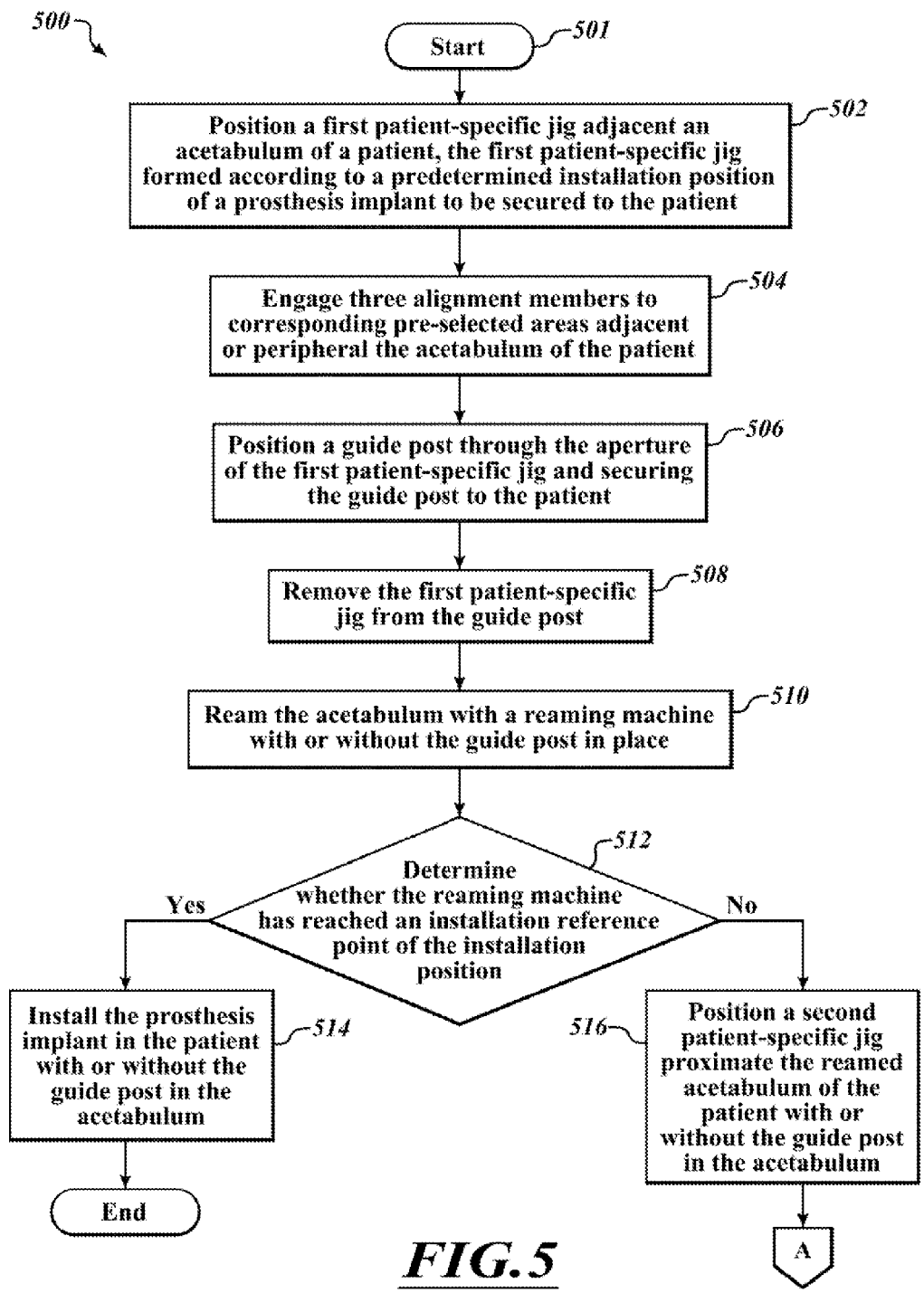
FIGS. 5 and 6 are flow diagrams illustrating steps for performing a joint replacement procedure, according to an aspect of the present invention.
Figure 6:
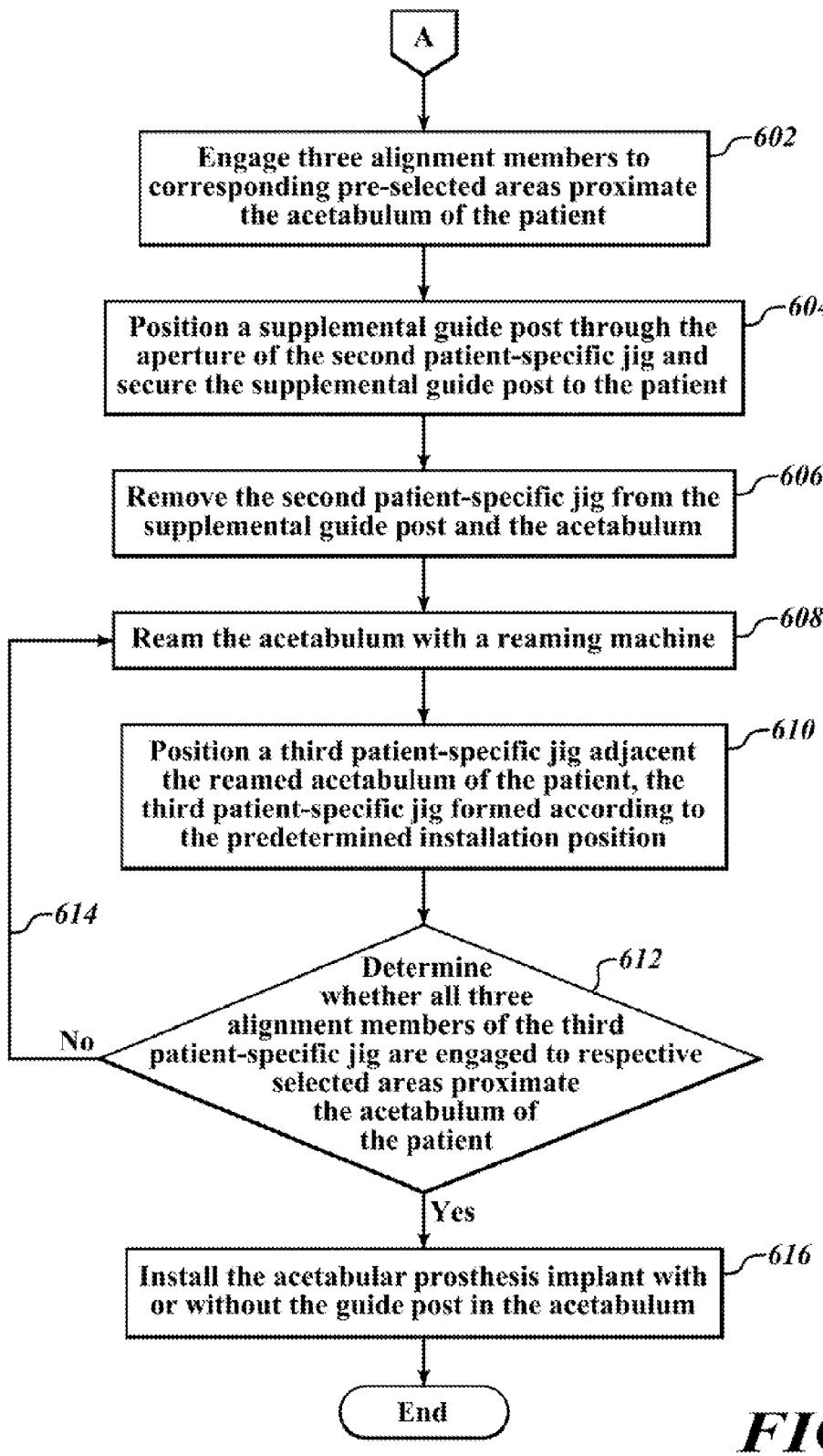

FIGS. 5 and 6 are flow diagrams of methods pertaining to operative surgery according to aspects of the present disclosure. The methods of FIGS. 5 and 6 may be carried out by a surgeon or by a machine, or by both. Moreover, the surgeon may utilize some or all of the devices discussed with reference to FIGS. 1-4A during surgery, such as viewing the preoperative images displayed on the display device while operating on a patient.

In FIG. 5, a method 500 according to an aspect starts at 501. At 502, a first patient-specific jig is positioned in an acetabulum of a patient. The first patient-specific jig is formed according to a predetermined installation position of a prosthesis implant to be secured to the patient. At 504, each of three alignment members is engaged with a corresponding pre-selected area on a coxal bone and adjacent the acetabulum of the patient. At 506, a guide post is positioned through the aperture of the first patient-specific jig and is secured into the coxal bone of the patient. At 508, the first patient-specific jig is removed from the guide post. At 510, bone material from the acetabulum is reamed with aid of a reaming machine. At 512, it is determined whether the reaming machine has reached an installation reference point of the installation position; this may be determined by the surgeon or by a measuring device or other device to determine the depth of bone that was reamed. If the reaming machine has reached an installation reference point, at 514 the guide post is removed and the prosthesis implant is installed in the patient, then ends. If the reaming machine has not reached an installation reference point, at 516 the guide post is removed and a second patient-specific jig is positioned in the reamed acetabulum of the patient, then to step 602 in FIG. 6. As further discussed below, in some aspects the guide post is not removed and remains secured to the patient until the prosthesis implant is installed.

At step 602, three alignment members of the second patient-specific jig are respectively engaged with predefined selected areas proximate the acetabulum of the patient. At 604, a supplemental guide post is positioned through the aperture of the second patient-specific jig and is secured into the coxal bone of the patient. At 606, the second patient-specific jig is removed from the supplemental guide post and the acetabulum. At 608, the acetabulum is reamed with aid of a reaming machine. In some instances the guide post can be removed prior to reaming and the sinus tract in the bone from the guide post is used as a visual guide to ream at a desired orientation and to a desired depth. At 610, a third patient-specific jig is positioned in the reamed acetabulum of the patient. At 612, it is determined whether all three alignment members of the third patient-specific jig are engaged to respective selected areas proximate the acetabulum of the patient. If yes, at 616 the supplemental guide post may or may not be removed and the prosthesis implant is secured to the reamed acetabulum and then ends. If no, the method returns to 608 and the operations are repeated until it is determined that all three alignment members of the third patient-specific jig are engaged to respective selected areas proximate the acetabulum of the patient so that the prosthesis implant may be installed in the patient.

Figure 7:
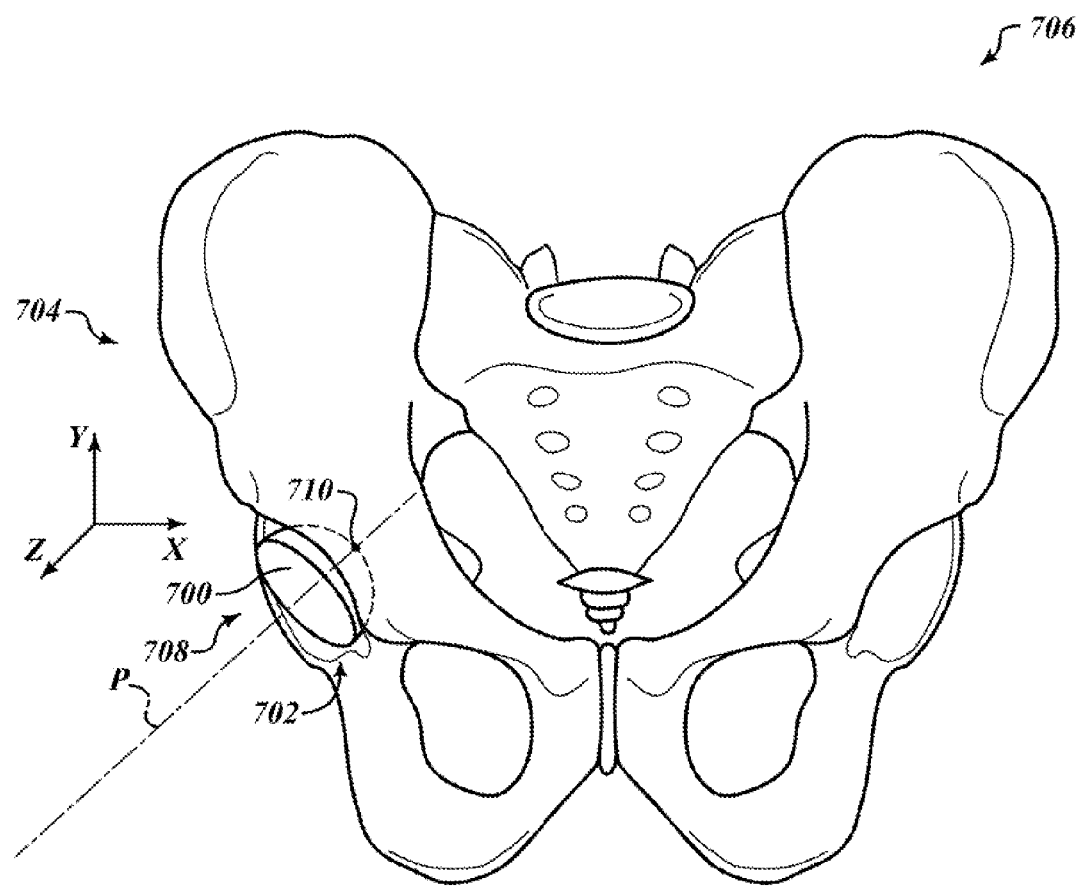
FIG. 7 is a front view of a pelvic bone.
Figure 8:
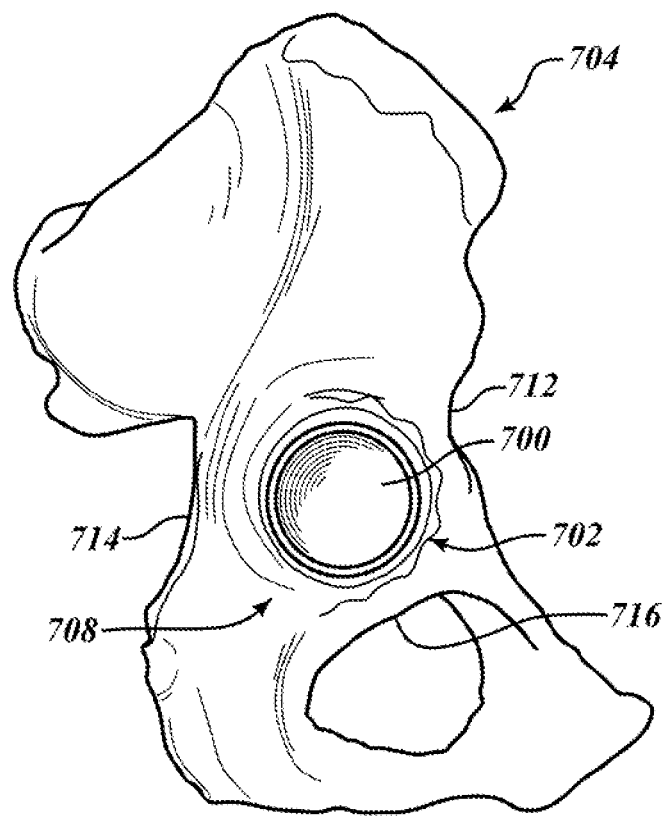
FIG. 8 is a top view of a prosthetic implant seated in the pelvic bone of FIG. 7.

FIGS. 7 and 8 show an acetabular component 700 oriented an in an acetabulum 702 of a coxal bone 704 of a pelvic bone 706. The acetabular component 700 is positioned according to an installation position 708, which is in part determined by a prescribed anteversion angle and a prescribed inclination angle of the acetabular component 700. FIG. 7 shows a front view of the pelvic bone 706 and the acetabular component 700 positioned in the acetabulum 702 of the patient's right coxal bone 704, and FIG. 8 shows a lateral view of the right coxal bone 704 with the acetabular component 700 positioned in the acetabulum 702. These figures illustrate the incorporation of steps discussed with reference to FIGS. 1-4A where the acetabular component 700 is a generated image that is superimposed over a generated image of bone structure (e.g., the coxal bone 704) of a patient to determine an installation position 708 of the acetabular component 700. Determining the prescribed anteversion angle and the prescribed inclination angle for a particular patient involves techniques and calculations that are known in the art, and thus, will not be described in detail. Although not necessarily part of the preoperative planning, for purposes of illustration an installation axis P is shown on FIG. 7

Once the installation position 708 is determined, a reference point 710 is established that represents a particular point in the coxal bone 704 of the patient for purposes of determining the depth to which a reaming machine will ream bone material, which will be further discussed below. The reference point 710 may be considered a point on the tangential plane of a hemispherical shaped surface, such as the outer surface shape of the acetabular component 700.

With continued reference to FIG. 8, the coxal bone 704 includes (among many others) a medial rim 712, a sciatic notch 714, and an obturator foramen 716, which all have various shapes and surfaces that are specific to each patient.

Figure 9A:
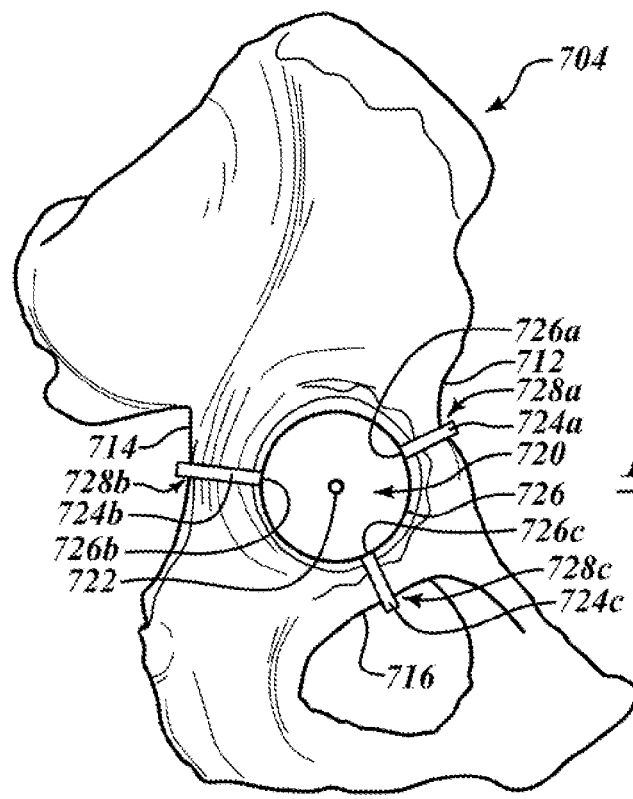
FIG. 9A is a top view of a patient-specific jig mounted on the pelvic bone of FIG. 7 according to one embodiment.
Figure 9B:
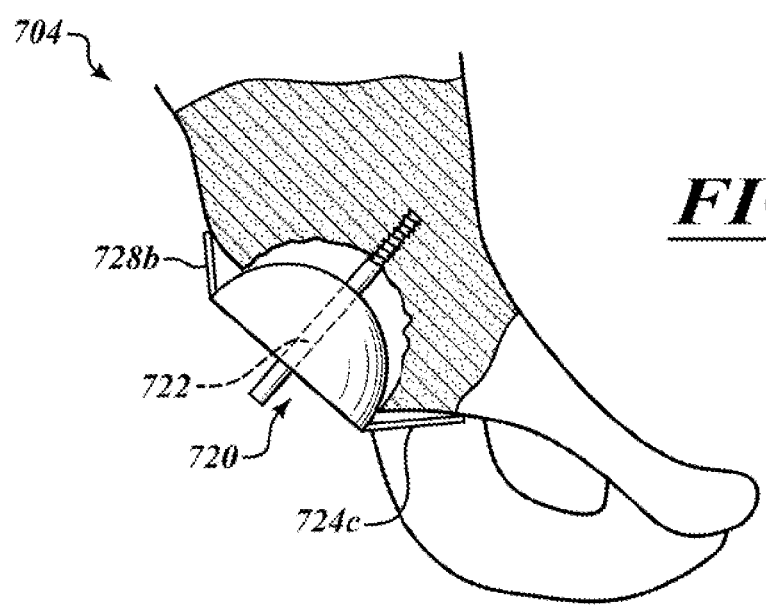
FIG. 9B is a partial cross-sectional view of the pelvic bone of FIG. 7 and a side view of the patient-specific jig of FIG. 9A.

FIGS. 9A and 9B show a patient-specific jig 720 oriented in the acetabulum 702 of the coxal bone 704 according to the installation position 708 of the acetabular component 702. These figures show a technique that incorporates steps of FIGS. 1-4A in that the patient-specific jig 720 is a generated image that is superimposed over the generated image of the bone structure of a patient. As a preliminary matter, the patient-specific jig 720 may be any one of the first, second, and third patient-specific jigs discussed with reference to FIGS. 10A-15B and elsewhere in this disclosure. FIGS. 9A and 9B are mere illustrations of one possible patient-specific jig 720.

The patient-specific jig 720 includes an aperture 722 and three alignment members 724a, 724b, 724c. The aperture 722 is formed through the patient-specific jig 720 at an angle that corresponds to the installation position 708 of the acetabular component 700. Depending upon the particular patient-specific jig 720 (i.e., the first, second, or third), the relative orientation of the aperture 722 may vary depending upon the required amount of bone to be removed and the particular required angle of a reaming head during operation, which is ultimately determined by the installation position 708 of the acetabular component 700. The angles of the various apertures for the various jigs are discussed further below.

The three alignment members 724a, 724b, 724c are attached to the patient-specific jig 720 at positions around a circumference end 726 (or distal end) of the patient-specific jig 720 depending upon the particular bone structure of the particular patient. The three alignment members 724a, 724b, 724c may be formed integral with the jig or may be attached to the jig with any suitable attachment means. The purpose of the three alignment members 724a, 724b, 724c help the surgeon: 1) determine the proper orientation of a guide post to be installed in the patient (FIGS. 13A and 15A), and/or 2) determine whether additional reaming of bone is necessary before utilizing another jig or before final installation of an acetabular component. In any event, depending on whether all of the three alignment members 724a, 724b, 724c of a particular patient-specific jig 720 are in contact with respective selected areas of the patient's bone during surgery when the particular jig is placed in the acetabulum 702, corresponding information is conveyed to the surgeon. The surgeon will be able to determine the next appropriate steps during surgery, as further described below.

The positions of the three alignment members 724a, 724b, 724c will depend on which particular jig (i.e., first, second, or third jigs) the three alignment members are attached to. However, the positions the three alignment members 724a, 724b, 724c may be the same on each jig depending on the preoperative requirements determined by the surgeon and the computing systems. In one example and as shown on FIG. 9B, the first alignment member 724a is attached to the patient-specific jig 720 at an attachment portion 726a, and the second alignment member 724b is attached to the patient-specific jig 720 at an attachment portion 726b, and the third alignment member 724c is attached to the patient-specific jig 720 at an attachment portion 726c. The position of the respective attachment portions 726a, 726b, 726c are determined during pre-operative imaging and planning steps. Accordingly, the three alignment members 724a, 724b, 724c extend from the circumference end 726 of the patient-specific jig 720 and are designed to contact certain selected areas of the coxal bone 704 depending on the bone structure of the patient. The first alignment member 724a contacts a selected area 728a of the medial rim 712. The second alignment member 724b contacts a selected area 728b of the sciatic notch 714. Finally, the third alignment member 724c contacts a selected area 728c inferiorally below the transverse acetabular ligament at the superior portion of the obturator foramen 716. In some instances, such as when using the second and third jigs, the contact between the alignment members and the respective selected areas is dependent upon whether the surgeon has reamed enough bone. If not, at least one of the alignment members will not be in contact with the respective selected area, indicating that more bone needs to be removed, as further discussed below.

Figure 10A:
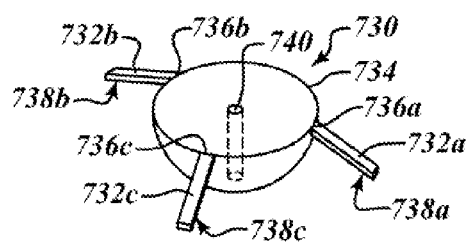
FIG. 10A is an isometric view of a first patient-specific jig according to one embodiment.
Figure 10B:
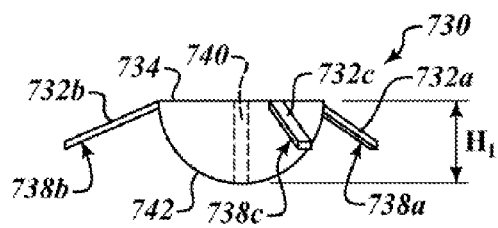
FIG. 10B is an elevational view of the first patient-specific jig of FIG. 10A.
Figure 11A:
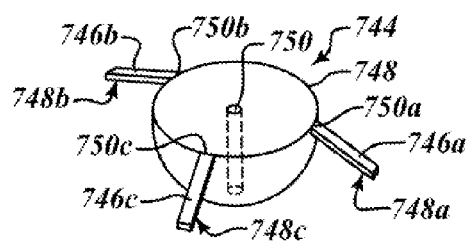
FIG. 11A is an isometric view of a second patient-specific jig according to one embodiment.
Figure 11B:
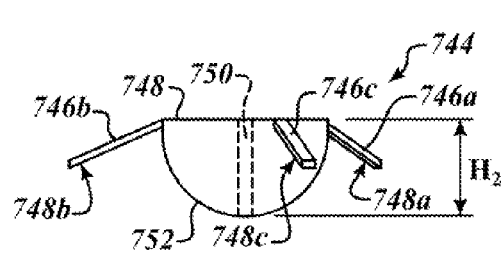
FIG. 11B is an elevational view of the second patient-specific jig of FIG. 11A.
Figure 12A:
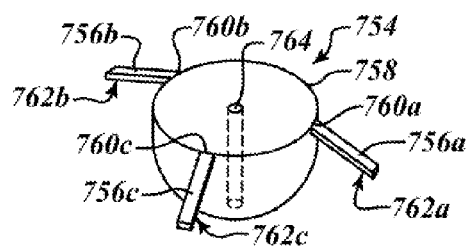
FIG. 12A is an isometric view of a third patient-specific jig according to one embodiment.
Figure 12B:
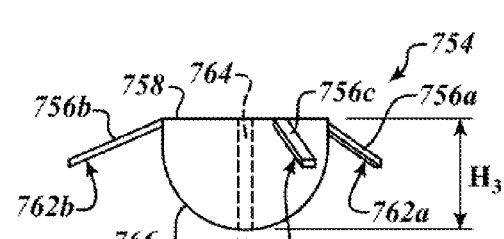
FIG. 12B is an elevational view of the third patient-specific jig of FIG. 8.

FIGS. 10A and 10B show a first patient-specific jig 730. FIGS. 11A and 11B show a second patient-specific jig 744. FIGS. 12A and 12B show a third patient-specific jig 754. These figures represent that the patient-specific jigs are generated images based on the installation position of the acetabulum component and based on the bone structure of the patient. Some or all of the patient-specific jigs are formed by a machine based on the generated images, as further discussed elsewhere in this disclosure. In some cases, only a first patient-specific jig is generated and created in instances where very little bone reaming is required, for example. In other instances, only a second or only a third patient-specific jig is utilized to accurately guide placement of an acetabular component without using the patient specific jig(s) to assist with removal of acetabular bone.

FIG. 10A shows an isometric view of a first patient-specific jig 730 and FIG. 10B shows a side elevational view of FIG. 10A. The first patient-specific jig 730 includes three alignment members 732a, 732b, 732c that extend from a circumference end 734 of the first patient-specific jig 730 at positions to contact certain selected areas of the coxal bone (see FIG. 9A (generically) and FIG. 13B (specifically)). The first alignment member 732a is attached to the patient-specific jig 730 at an attachment portion 736a, and the second alignment member 732b is attached to the first patient-specific jig 730 at an attachment portion 736b, and the third alignment member 732c is attached to the patient-specific jig 730 at an attachment portion 736c. The angle and position of each alignment member 732a, 732b, 732c relative to the circumference end 734 is determined according to the particular position and surface of the selected areas of the coxal bone of the patient that the alignment members 732a, 732b, 732c are designed to contact during use of the first patient-specific jig 730 during operation. Each alignment member 732a, 732b, 732c includes an engagement portion 738a, 738b, 738c, respectively, which is the portion of the alignment member that contacts respective selected areas of the coxal bone 704. See FIGS. 13A and 13B for illustrations of the position of each alignment members 732a, 732b, 732c relative to the first patient-specific jig 730 and the selected areas of the patient's coxal bone 704.

Figure 13A:
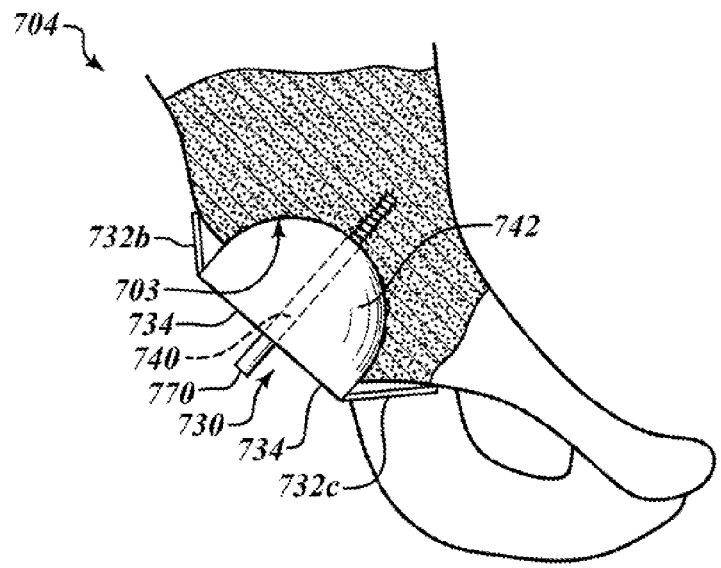
FIG. 13A is a side view of a first patient-specific jig positioned in an acetabulum and a guide post positioned through said jig and secured to the acetabulum.

The first patient-specific jig 730 includes an aperture 740 that extends from a reference end 742 to the circumference end 734 of the first patient-specific jig 730. The aperture 740 is sized and configured to receive a guide post positioned in a patient (FIG. 13A). As further described below, the guide post is positioned according to the installation position 708 of the acetabular component 700 (FIGS. 7 and 8). The first patient-specific jig 730 includes a height H1, which is selected so that the reference end 742 does not contact an unreamed acetabulum at the beginning stages of surgery. This is discussed further below.

FIG. 11A shows an isometric view of a second patient-specific jig 744 and FIG. 11B shows a side elevational view of FIG. 11A. The second patient-specific jig 744 includes three alignment members 746a, 746b, 746c that extend from a circumference end 748 of the second patient-specific jig 744 at positions to contact certain selected areas of the coxal bone (see FIG. 9A (generically) and FIG. 15B (specifically)). The alignment members 746a, 746b, 746c are attached to the second patient-specific jig 744 at respective attachment portions 750a, 750b, 750c, similar to the first patient-specific jig 730. The angle and position of each alignment member 746a, 746b, 746c relative to the circumference end 748 is determined according to the particular position and surface of the selected areas of the coxal bone of the patient that the alignment members 746a, 746b, 746c are designed to contact during use of the second patient-specific jig 744 during operation. The angle and position of each alignment member 746a, 746b, 746c may be the same as or different than that of the alignment members of the first patient-specific jig 730 of FIG. 10A. Each alignment member 746a, 746b, 746c includes an engagement portion 748a, 748b, 748c, respectively, which is the portion of the alignment member that contacts respective selected areas of the coxal bone 704. See FIGS. 15A and 15B for illustrations of the position of each alignment member 746a, 746b, 746c relative to the second patient-specific jig 744 and the selected areas of the patient's coxal bone 704.

Figure 15A:
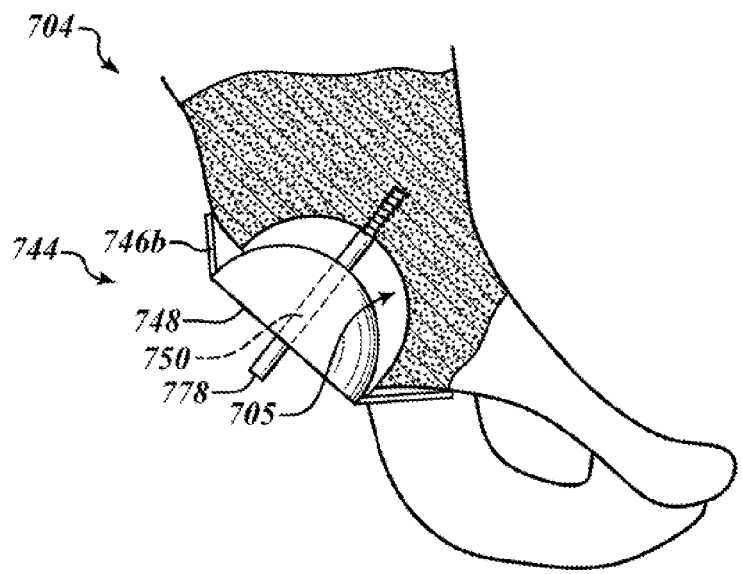
FIG. 15A is a side view of a second patient-specific jig positioned in an acetabulum and a supplemental guide post positioned through said jig and secured to the acetabulum.

The second patient-specific jig 744 includes an aperture 750 that extends from a reference end 752 to the circumference end 748 of the second patient-specific jig 744. The aperture 750 is sized and configured to receive a supplemental guide post positioned in a patient (FIG. 15A). As further described below, the supplemental guide post is positioned according to the installation position 708 of the acetabular component 700 (FIGS. 7 and 8). The second patient-specific jig 744 includes a height H2, which is selected so that, if the reference end 752 contacts a reamed acetabulum, and if at least one of the alignment members 746a, 746b, 746c is not in contact with a respective selected area of the coxal bone, the surgeon will know that additional reaming is necessary before installing the supplemental guide post and placing the final acetabular prosthesis. This is discussed further below. Understandably, height H2 can be greater than height H1, in part because bone is reamed between usage of the first and second jigs.

FIG. 12A shows an isometric view of a third patient-specific jig 754 and FIG. 12B shows a side elevational view of FIG. 12A. The third patient-specific jig 754 includes three alignment members 756a, 756b, 756c that extend from a circumference end 758 of the third patient-specific jig 754 at positions to contact certain selected areas of the coxal bone (see FIG. 9A (generically) and FIG. 17B (specifically)). The alignment members 756a, 756b, 756c are attached to the third patient-specific jig 754 at respective attachment portions 760a, 760b, 760c, similar to the first patient-specific jig 730. The angle and position of each alignment member 756a, 756b, 756c relative to the circumference end 758 is determined according to the particular position and surface of the selected areas of the coxal bone of the patient that the alignment members 756a, 756b, 756c are designed contact during use of the third patient-specific jig 754 during operation. The angle and position of each alignment member 756a, 756b, 756c may be the same or different to that of the alignment members of the first and second patient-specific jigs of FIGS. 10A and 11A. Each alignment member 756a, 756b, 756c includes an engagement portion 762a, 762b, 762c, respectively, which is the portion of the alignment member that contacts respective selected areas of the coxal bone 704. See FIGS. 17A and 17B for illustrations of the position of each alignment members 756a, 756b, 756c relative to the third patient-specific jig 754 and the selected areas of the patient's coxal bone 704.

Figure 17A:
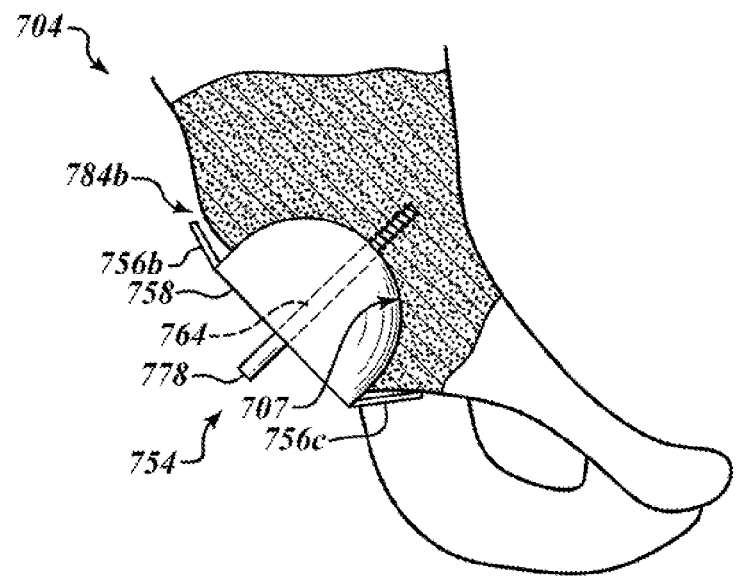
FIG. 17A is a side view of a third patient-specific jig positioned in the acetabulum and the supplemental guide post of FIG. 15A.

The third patient-specific jig 754 includes an aperture 764 that extends from a reference end 766 to the circumference end 758 of the third patient-specific jig 754. The aperture 764 is sized and configured to receive the supplemental guide post positioned in a patient (FIG. 17A). As further described below, the supplemental guide post is positioned according to the installation position 708 of the acetabular component 700 (FIGS. 7 and 8). The third patient-specific jig 754 includes a height H3, which is selected so that, if the reference end 766 contacts a reamed acetabulum, thereby causing at least one of the alignment members 756a, 756b, 756c to not be in contact with a respective selected area of the coxal bone, the surgeon will know that additional reaming is necessary before installing the acetabular component 700 in the patient. This is discussed further below. Understandably, height H3 can be greater than height H2 because bone is reamed between usage of the second and third jigs, and because the second patient-specific jig is used for purposes of positioning the supplemental guide post while the third patient-specific jig is used for purposes of determining whether additional reaming is necessary before installing the acetabular component 700 in the patient.

It will be appreciated that each or all of the alignment members of any one of the patient-specific jigs may be formed in various configuration and shapes. For example, an alignment member may be an arc shaped or other non-linear shaped member, or it may have two or more angles surfaces. The exact shape, position, and alignment of each alignment member is determined by the surgeon and the computing system during preoperative planning depending upon the specific bone structure of the patient and the installation position of the acetabulum component.

Figure 13B:
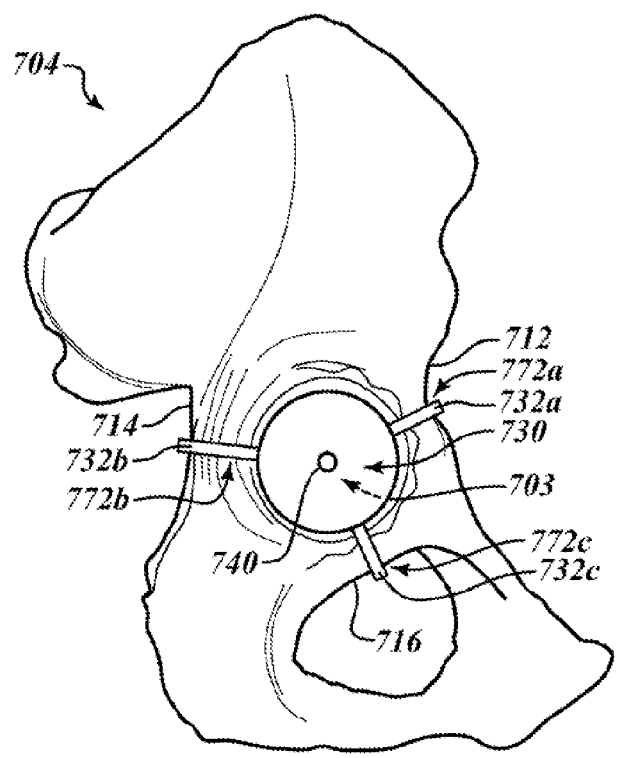
FIG. 13B is a side view of the pelvic bone showing the first patient-specific jig positioned in the acetabulum.
Figure 14:
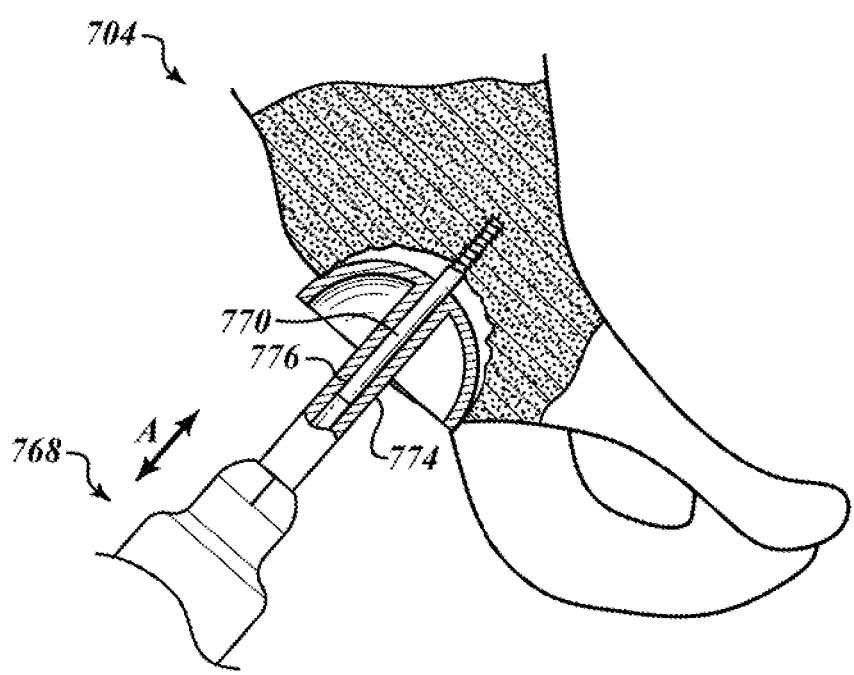
FIG. 14 is a cross-sectional view of a reaming tool positioned in the acetabulum.

FIGS. 13A and 13B show the first patient-specific jig 730 positioned in an un-reamed acetabulum 703 of the patient, and FIG. 14 shows a reaming tool 768 positioned in the acetabulum 703 and ready to ream bone material. These figures show a technique that incorporates the preoperative steps of FIGS. 1-4A in that the first patient-specific jig 730 and a guide post 770 are generated images that are superimposed over the generated image of the bone structure of a patient. These figures also show a technique that incorporates the operative steps practiced by a surgeon on a patient, such as described with reference to FIGS. 5 and 6.

During preoperative planning and with reference to FIGS. 9A and 9B, a generated image of an acetabular component 700 is imposed over the bone structure image, which ultimately shows the installation position 708 of the acetabular component 700. Based on such installation position 708, the computer system determines, with input from the surgeon, the exact position of the guide post 770 to be installed in the patient during early stages of operation. The guide post 770 will be the guide for the position of the first patient-specific jig 730 and the reaming machine 768. Preferably, the guide post 770 is positioned substantially perpendicular to a central axis of the acetabular component 700 to be later installed in the patient; however, the angle of the guide post 770 relative to the acetabular component 700 may vary depending upon the preoperative surgery analysis by the computer system and the surgeon based on patient requirements. Once the orientation of the guide post 770 is established and displayed as a generated image, an image is generated of the first patient-specific jig 730. As noted above, the purpose of the first patient-specific jig 730 is to establish the exact position of the guide post 770 to be installed in the patient during surgery. Accordingly, the reference end 742 of the first patient-specific jig 730 is designed to make contact with the un-reamed acetabulum 703. The three alignment members 732a, 732b, 732c are designed to contact respective selected areas of the coxal bone 704 adjacent the acetabulum 703.

With particular reference to FIG. 13B, during surgery the surgeon inserts the first patient-specific jig 730 into the acetabulum 703 and rotates or otherwise orients the first patient-specific jig 730 in the patient until all three alignment members 732a, 732b, 732c are in contact with respective selected areas 772a, 772b, 772c of the coxal bone 704. Once the first patient-specific jig 730 is properly oriented, the surgeon inserts the guide post 770 through the aperture 740 and guide post 770, which may be a threaded pin, and may be drilled into the bone (typically 2 mm to 20 mm deep). Thus, the guide post 770 will be installed at the exact position determined during preoperative planning and according to the installation position of the acetabular component 700. The first patient-specific jig 730 may then be removed and a reaming machine 768 may be used to remove bone material from the patient, either over the guide post or without it in place.

FIG. 14 illustrates the reaming machine 768 used for such purpose. The reaming machine 768 includes a reaming head 774, which may be a detachable head of a selected size corresponding to the size of the acetabular component 700 to be installed. The reaming head 774 includes a guide aperture 776 that slidably receives the guide post 770. The reaming head 774 reams bone with a consistent axial motion in a direction depicted by Arrow A because the guide aperture 776 includes a central axis coextensive with a central axis of the guide post 770 and because the guide aperture 776 closely receives the guide post 770. In some embodiments, the reaming may be cannulated while in other embodiments, the reaming may not be cannulated. In some embodiments, The surgeon may remove the guide post prior to reaming and use the visible pilot hole as a visual guide to center the reamers that can be used by traditional means without cannulated reaming. Such reaming heads with a guide aperture and methods of using such reaming heads with a guide post in a patient are well known in the art and will not be described in greater detail.

Figure 15B:
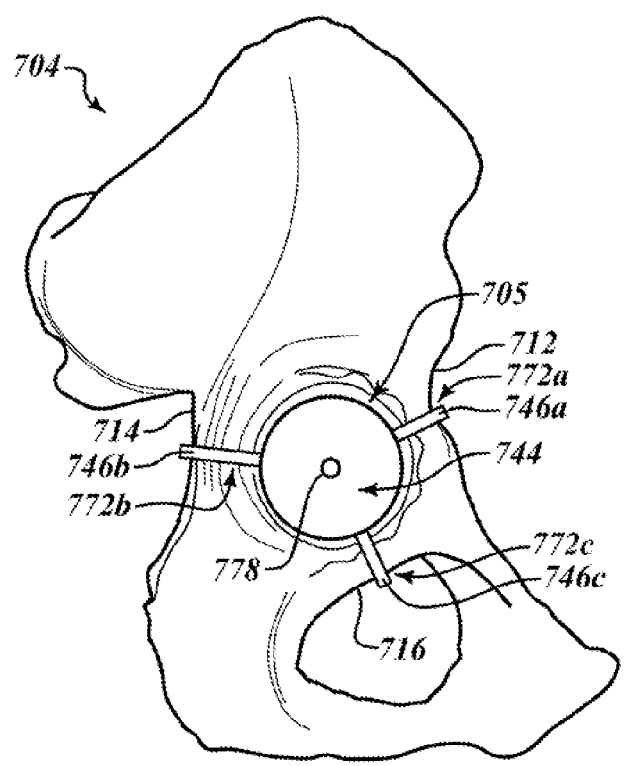
FIG. 15B is a side view of the pelvic bone showing the second patient-specific jig positioned in the acetabulum 15A.
Figure 16:
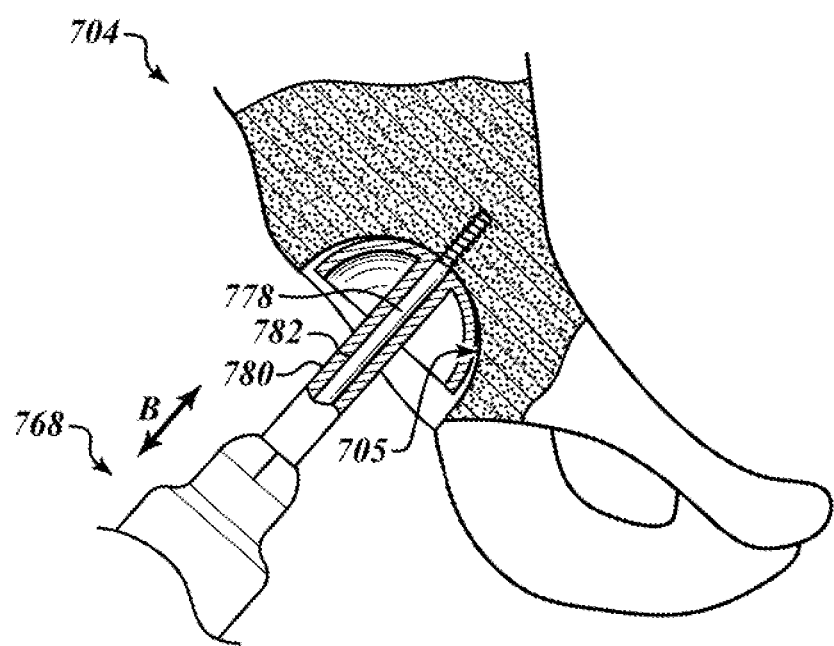
FIG. 16 is a cross-sectional view of a reaming tool positioned in the acetabulum.

FIGS. 15A and 15B show the second patient-specific jig 744 positioned in a reamed acetabulum 705 of the patient, and FIG. 16 shows a reaming tool 768 ready to ream additional bone material. These figures show a technique that incorporates the preoperative steps in that the second patient-specific jig 744 is a generated image that is superimposed over the generated image of the bone structure of a patient. These figures also show a technique that incorporates the operative steps practiced by a surgeon on a patient.

FIG. 15A shows the reamed acetabulum 705 as the result of the surgeon reaming a portion of the acetabulum 703 to a desired depth. In some instances, the surgeon will ream a couple millimeters of bone and will have reached the reference point 710 (FIG. 7) such that bone reaming is completed and the acetabular component 700 can be installed in the patient. In other instances, additional bone reaming is necessary to a depth depending upon the installation position 708 for a particular patient as determined during preoperative planning. When it is determined that additional bone reaming is necessary, in some instances the guide post 770 of FIG. 13A remains installed in the patient and the second patient-specific jig 744 is utilized to determine if additional bone reaming is necessary; this is accomplished by inserting the second patient-specific jig 744 into the reamed acetabulum 705. In some embodiments, the second patient-specific jig 744 is inserted over the guide post 770 while in other embodiments, the guide post 770 may be removed before inserting the second patient specific jig 774. With the second patient specific jig in the acetabulum 705, the surgeon may determine whether the three alignment member 746a, 746b, 746c are all in contact with selected areas 772a, 772b, 772c of the coxal bone 704. If not, in some embodiments, before further reaming, the surgeon may reinsert the guide post 770 into the bone and advance it or drill it further into the bone. The surgeon may then remove the guide post 770 and may utilize the reaming machine 768 of FIG. 14 and ream additional bone material. The surgeon may continue to check the depth of the reamed acetabulum 705 by utilizing the second patient-specific jig 744 as noted above until all three alignment members 746a, 746b, 746c are in contact with the selected areas 772a, 772b, 772c of the coxal bone 704. Once this is achieved, the surgeon will know with accurate precision that the reference point 710 has been reached and at the desired angle for accurate installation of the acetabular component 700 in the patient. The surgeon may then install the acetabular component 700 in the patient utilizing known techniques in the art. In the current method, a guide post may be utilized over which the acetabular component 700 may be more accurately placed than with standard techniques.

In other instances and where additional bone reaming is necessary but at a different angle than with respect to FIG. 14 according to preoperative planning, the guide post 770 is removed from the patient and a supplemental guide post 778 is installed in the patient to guide the reaming machine 768 at a different angle than the original guide post 770. In some instances the supplemental guide post 778 may be removed prior to reaming and the sinus tract in bone may guide the surgeon to ream at an appropriate angle and to an appropriate depth. Such operative steps are determined by the surgeon, with the use of the computing system, during preoperative planning. For purposes of illustration and as one example, FIGS. 15A and 15B show the supplemental guide post 778 installed in the patient at a different angle than the guide post 770 of FIGS. 13A and 14. Accordingly, once the bone is reamed as described with reference to FIG. 14, the guide post 770 is removed and the second patient-specific jig 744 is placed into the reamed acetabulum 705. Similar to the first patient-specific jig 730, the second patient-specific jig 744 is utilized to determine the orientation of the supplemental guide post 778 to be installed in the patient. Thus, the surgeon inserts the second patient-specific jig 744 into the reamed acetabulum 705 and rotates or otherwise orients the second patient-specific jig 744 in the patient until all three alignment members 746a, 746b, 746c are in contact with respective selected areas 772a, 772b, 772c of the coxal bone 704, as depicted on FIGS. 15A and 15B. Once the second patient-specific jig 744 is properly oriented, the surgeon inserts the supplemental guide post 778 through the aperture 750 and the threads of the supplemental guide post 778 engage the bone. Thus, the supplemental guide post 778 will be installed at the exact position determined during preoperative planning and according to the installation position of the acetabular component 700. The second patient-specific jig 774 may then be removed and a reaming machine 768 may be used to remove additional bone material from the patient, with or without the guide post in place.

FIG. 16 illustrates the reaming machine 768 used for such purpose. The reaming machine 768 includes a supplemental reaming head 780, which may be a detachable head of a selected size corresponding to the size of the acetabular component 700 to be installed. The supplemental reaming head 780 may be smaller in size than the reaming head 774 of FIG. 14, or it may be the same size. The supplemental reaming head 780 may include a guide aperture 782 that slidably receives the supplemental guide post 778. The supplemental reaming head 780 reams bone with a consistent axial motion in a direction depicted by Arrow B because the guide aperture 782 includes a central axis coextensive with a central axis of the supplemental guide post 778 and because the guide aperture 782 closely receives the supplemental guide post 778. Such reaming heads having a guide aperture are well known in the art and will not be described in greater detail.

Figure 17B:
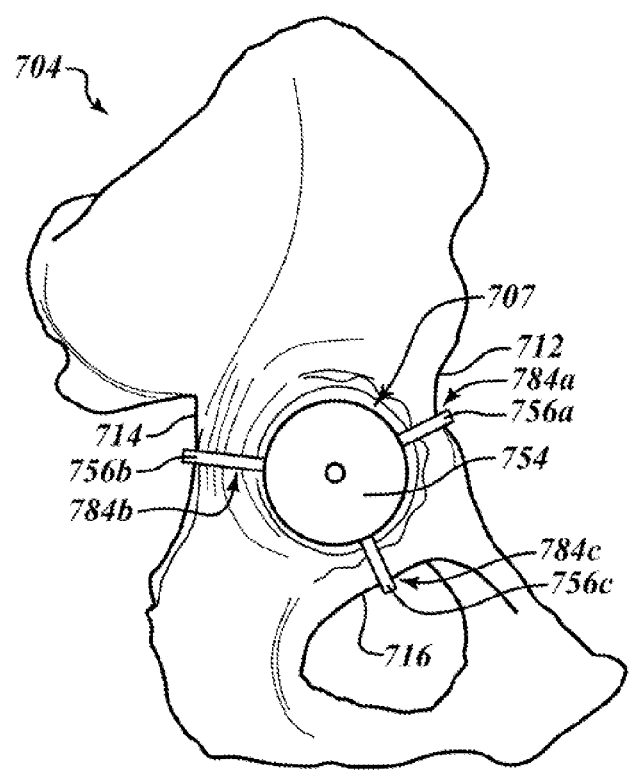
FIG. 17B is a top view of the third patient-specific jig positioned in the acetabulum as shown in FIG. 17A.

FIGS. 17A and 17B show the third patient-specific jig 754 positioned in a reamed acetabulum 707 of the patient. These figures show a technique that incorporates the preoperative steps of FIGS. 1-4A in that the third patient-specific jig 754 is a generated image that is superimposed over the generated image of the bone structure of a patient. These figures also show a technique that incorporates the operative steps practiced by a surgeon on a patient disclosed herein.

FIG. 17A shows a reamed acetabulum 707 as the result of the surgeon reaming a portion of the acetabulum 705 to a desired depth, as discussed with reference to FIG. 16. In some instances, the surgeon will ream one or two millimeters of bone and utilize the third patient-specific jig 754 to determine whether additional bone reaming is necessary before final installation of the acetabular component in the patient, as determined during preoperative planning. Thus, the surgeon inserts the third patient-specific jig 754 into the reamed acetabulum 707. If all three alignment members 756a, 756b, 756c are in contact with respective selected areas 784a, 784b, 784c of the coxal bone 704, then the third patient-specific jig 754 has indicated that the reference point 710 of the installation position 708 has been reached, and therefore, bone reaming is completed.

The surgeon will then install the acetabular component 700 according to known techniques or over a supplemental guide post using a cannulated acetabular impactor and mallet device as described herein. For purposes of discussion, FIG. 17A shows that alignment member 756b is not in contact with the selected area 784b adjacent to the native acetabulum. As such, the illustrated third patient-specific jig 754 indicates that the reference point 710 has not been reached, and, therefore, additional bone reaming is necessary. Accordingly, the surgeon reams bone with the reaming head 780, utilizing the supplemental guide post 778 pilot hole or sinus tract from the removed guide post as a guide member, and then inserts the third patient-specific jig 754 to determine whether all three alignment members 756a, 756b, 756c are in contact with the coxal bone 704 and the reference point 710 (FIG. 7) has been reached by the supplemental reaming head 780. These processes continue until the acetabulum is reamed to the desired depth of the reference point, at which point the surgeon installs the acetabular component 700 in the patient, as shown on FIG. 8.

FIGS. 18-22 show aspects of the present disclosure in which an impactor tool 800 is used to assist with installation of an acetabular component 700 in a reamed acetabulum 705 or 707. Typically, a reamed acetabulum is reamed to have a radius slightly smaller than the radius of the acetabular component for a tight fit configuration. As such, the surgeon typically utilizes a mallet or other tool to impact the acetabular component into its final position.

The impactor tool 800 includes a head 802 and a handle 804. The head 802 includes a guide aperture 806 having a central axis X. During surgery and once the acetabulum is reamed to a desired depth, the acetabular component 700 is partially inserted into the reamed acetabulum. An elongated guide post 808 is installed in the coxal bone 704 and extends through a hole in the acetabular component 700, as known in the art. A cannulated acetabular impactor device 810 includes a cannulated channel 812 that receives the elongated guide post 808; the cannulated acetabular impactor device 810 may be threaded or slidably received over the elongated guide post 808. The cannulated acetabular impactor device 810 includes a distal end 814 biased against the cup portion of the acetabular component 700, and a proximal end 816 with a surface 818 to be impacted by the impactor tool 800. The distal end of the cannulated impactor tool may be cylindrical, hemispherical, or any other shape. The distal end may simply abut the acetabular prosthesis or alternatively thread into the acetabular prosthesis. The distal end of the impactor tool may be one piece or more than one piece. The guide aperture 806 of the impactor tool 800 slidably receives a portion of the guide post 808. The proximal portion of an impactor tool may have a cannulated opening for the guide post in some embodiments. In some embodiments, the proximal portion of the impactor tool may not have a cannulated opening. The proximal portion of an impactor tool may be one piece or more than one piece.

During installation of the acetabular component 700, the surgeon holds the handle 804 and slidably engages the guide aperture 806 of the impactor tool 800 with the guide post 808. The surgeon then repeatedly impacts the surface 818 of the proximal end 816 of the cannulated acetabular impactor device 810 with the impactor tool 800, causing an impacting force against the acetabular component 700, until the acetabular component 700 is in its final position. Typically several impacts with the impactor tool 800 will suffice, and typically the surgeon can hear when the acetabular component 700 is seated flush against the acetabulum in its final position. One advantage of the impactor tool 800 is that impact against the elongated member 810 (and ultimately the acetabular component 700) occurs at approximately the same impact location upon each repeated impact with the tool 800. Typically, the surgeon uses a mallet or hammer without the assistance of any guidance, which can result in improper installation of the acetabular component 700. The guide aperture 806 of the impactor tool 800 ensures repeatable impact location and position of the impactor tool 800, which reduces or eliminates the possibility for human error during repeated impacts with a mallet or hammer.

Figure 23A:
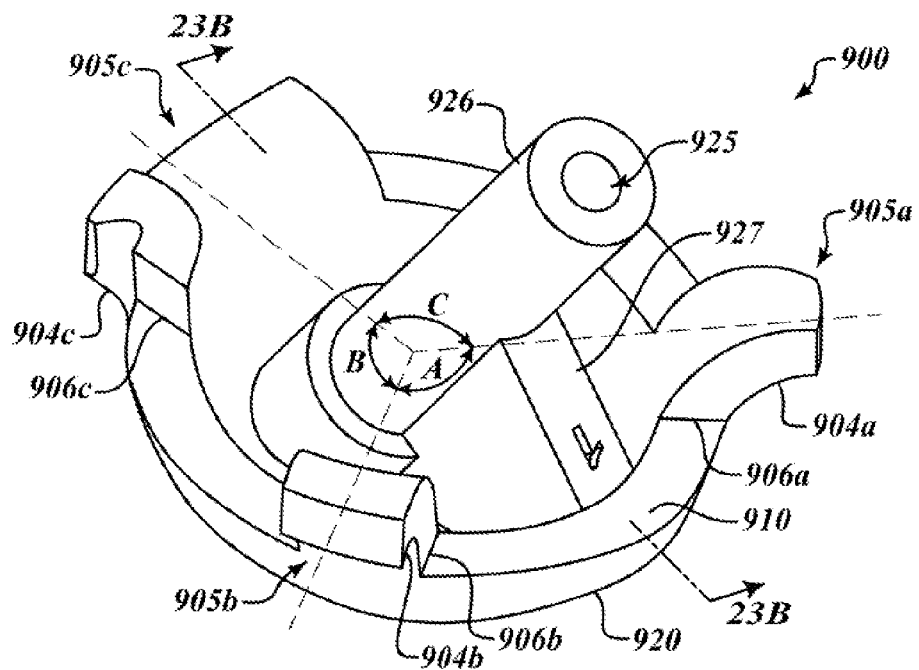
FIG. 23A is a perspective view of a patient specific jig.
Figure 23B:
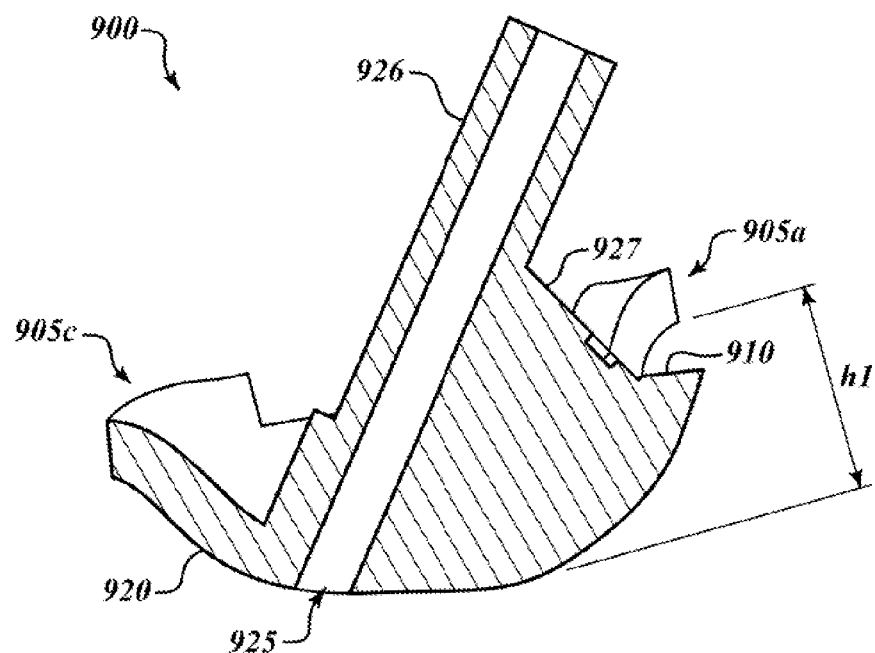
FIG. 23B is a cross-sectional view of the patient specific jig of FIG. 23A.
Figure 24A:
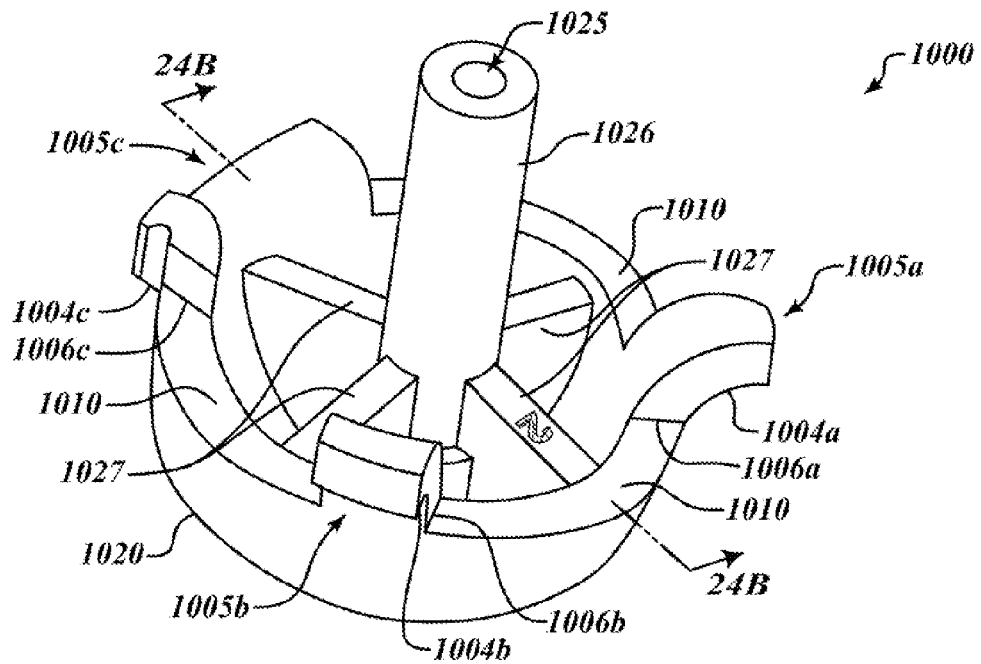
FIG. 24A is a perspective view of a patient specific jig.
Figure 24B:
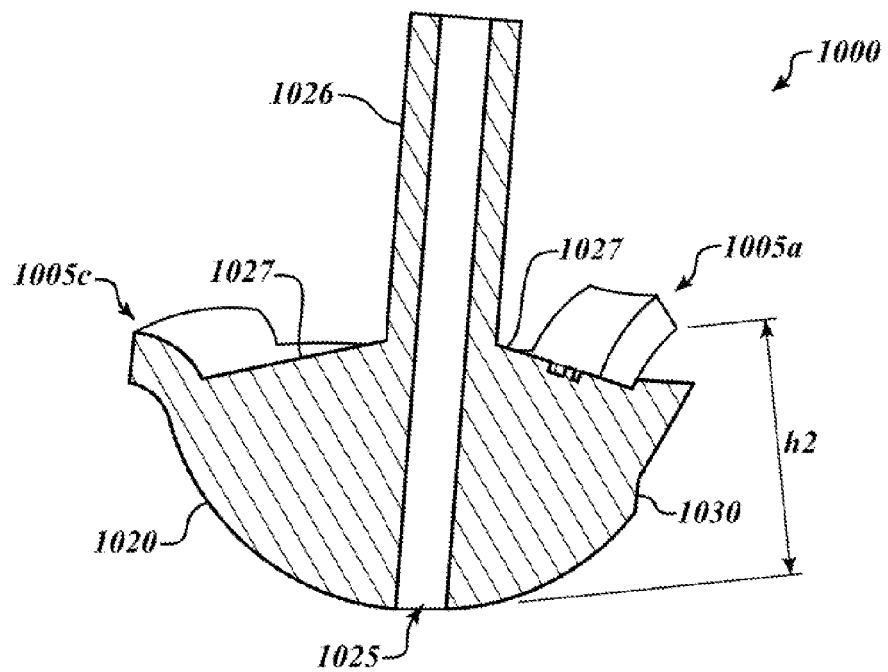
FIG. 24B is a cross-sectional view of the patient specific jig of FIG. 24A.
Figure 25A:
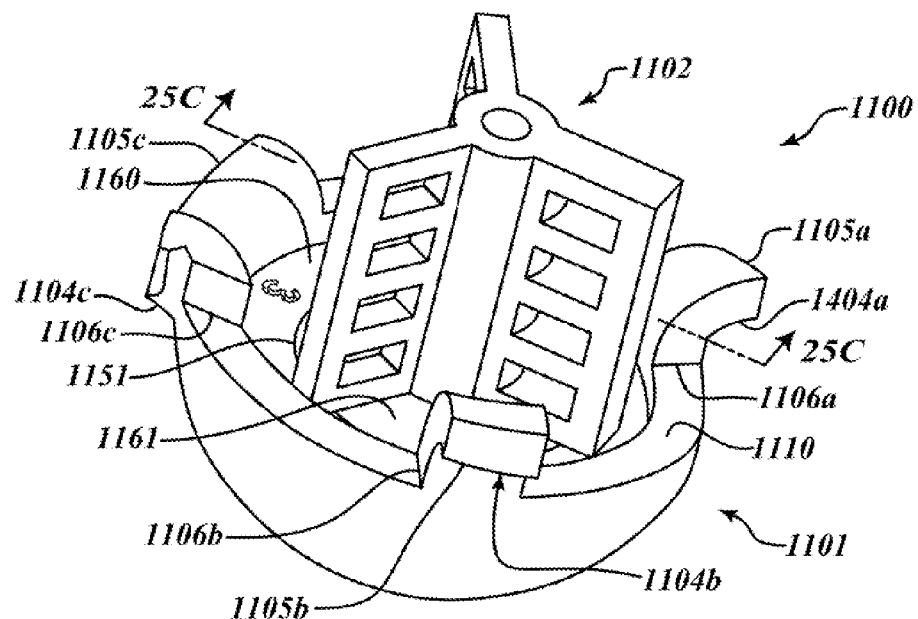
FIG. 25A is a perspective view of a patient specific jig.
Figure 25B:
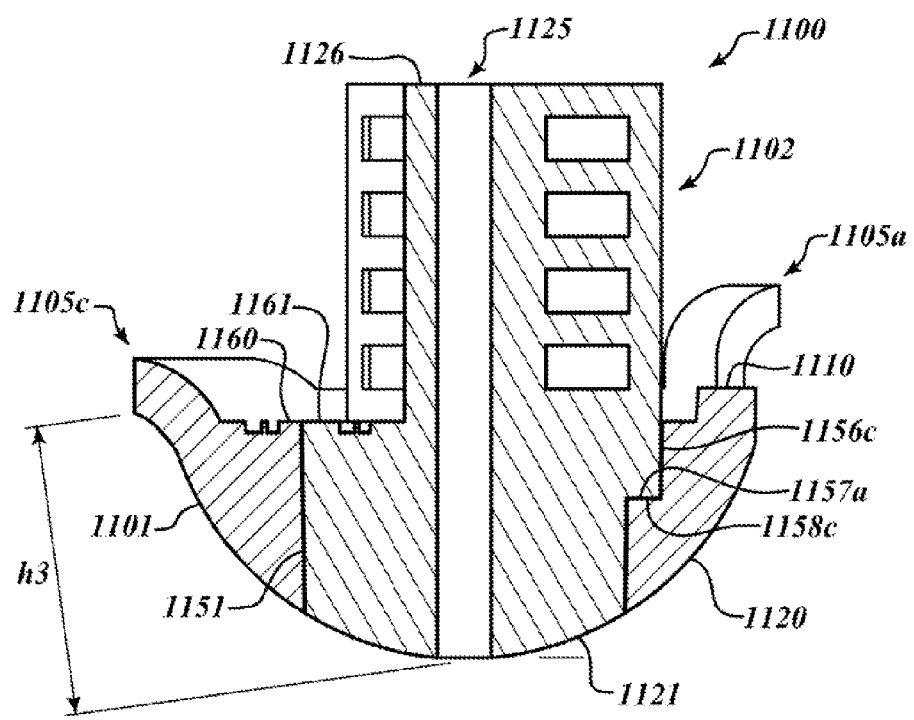
FIG. 25B is a cross-sectional view of the patient specific jig of FIG. 25A.

According to an alternate embodiment, FIGS. 23A and 23B show a first patient-specific jig 900; FIGS. 24A and 24B show a second patient-specific jig 1000; and FIGS. 25A and 25B show a third patient-specific jig assembly 1100. These figures show computer-generated images that represent the patient-specific jigs. They are created based on the installation position of the acetabulum component and the bone structure of the patient. Some of the information for generating the patient-specific jigs may be derived from data gathered using two-dimensional and/or three-dimensional imaging techniques.

The physical patient-specific jigs can be formed based on the generated images, as further discussed elsewhere in this disclosure. In some cases, only a first patient-specific jig is generated and created; for example, in instances where very little bone reaming is required. In some embodiments, physical jigs are created using a machining process, such as, an additive manufacturing process, a subtractive process, or a combination of additive and subtractive manufacturing processes.

FIG. 23A shows an isometric view of a first patient-specific jig 900; and FIG. 23B shows a cross-sectional view of a first patient-specific jig 900. The first patient-specific jig 900 may include three alignment members 905a, 905b, 905c that extend from a circumference end 910 of the first patient-specific jig 900. The alignment members are positioned to contact certain selected areas of the coxal bone (see, for example, FIG. 9A (generically) and FIG. 13B (specifically) and their associated text). The first alignment member 905a is attached to the patient-specific jig 900 at an attachment portion 906a; the second alignment member 905b is attached to the first patient-specific jig 900 at an attachment portion 906b; and the third alignment member 905c is attached to the patient-specific jig 900 at an attachment portion 906c. The angle and position of each alignment member 905a, 905b, 905c relative to the circumference end 910 is determined according to the particular position and surface of the selected areas of the coxal bone of the patient that the alignment members 905a, 905b, 905c contact during a procedure. Each alignment member 905a, 905b, 905c includes an engagement portion 904a, 904b, 904c, respectively, that contacts the coxal bone.

The engagement portion 904a of the first alignment member 905a may be contoured or shaped to abut the surface of the medial rim of the patient; the engagement portion 904b of the second alignment member 905b may be contoured or shaped to abut the surface of the sciatic notch of the patient; and the engagement portion 904c of the third alignment member 905c may be contoured or shaped to abut the surface of the acetabular notch of the patient. The angle A between the first alignment member 905a and the second alignment member 905b may be approximately 105 degrees; the angle B between the second and third alignment members 905b, 905c may be approximately 120 degrees; and the angle C between the third and first alignment members 905c, 905a may be approximately 135 degrees. See FIGS. 13A and 13B for exemplary illustrations of the position of alignment members relative to a first patient-specific jig and the selected areas of a patient's coxal bone.

The first patient-specific jig 900 can include an aperture 925 that extends from a reference end 920, through a collar 926, to a distal end of the first patient-specific jig 900. The illustrated aperture 925 is sized and configured to receive a guide post positioned in a patient (for example, as shown in FIG. 13A and described in the associated text). The collar 926 may be supported by one or more supports, such as support 927, which may extend from the collar 926 to the circumference of the jig. As further described below, the guide post is positioned according to an installation position, for example, installation position 708 of the acetabular component 700 (FIGS. 7 and 8). The first patient-specific jig 900 includes a height h1, which may be selected so that the reference end 920 may not contact an unreamed acetabulum at the beginning stages of surgery. In some embodiments, the reference end 920 may not contact the undreamed acetabulum. This is discussed further below.

FIG. 24A shows an isometric view of a second patient-specific jig 1000 and FIG. 24B shows a cross-sectional view of the second patient-specific jig 1000. The second patient-specific jig 1000 includes three alignment members 1005a, 1005b, 1005c that extend from a circumference end 1010 of the second patient-specific jig 1000 at positions selected to contact certain areas of the coxal bone (see, for example, FIG. 9A (generically) and FIG. 15B (specifically) and accompanying text). The alignment members 1005a, 1005b, 1005c are attached to the second patient-specific jig 1000 at respective attachment portions 1006a, 1006b, 1006c, similar to the first patient-specific jig 900. The angle and position of each alignment member 1005a, 1005b, 1005c relative to the circumference end 1010 is determined according to the particular position and surface of the selected areas of the coxal bone or other anatomy or anatomic structure of the patient that the alignment members 1005a, 1005b, 1005c are designed to contact during use of the second patient-specific jig 900. The angle and position of each alignment member 1005a, 1005b, 1005c may be the same as or different than that of the alignment members of the first patient-specific jig 900. Each alignment member 1005a, 1005b, 1005c includes an engagement portion 1004a, 1004b, 1004c, respectively, that contacts selected areas of a coxal bone. For example, see FIGS. 15A and 15B for illustrations of the position of alignment members relative to a second patient-specific jig and selected areas of a patient's coxal bone.

The second patient-specific jig 1000 can include an aperture 1025 that extends from a reference end 1020 through a collar 1026, to a distal end of the collar 1026 of the first patient-specific jig 1000. The illustrated aperture 1025 is sized and configured to receive a supplemental guide post positioned in a patient (see, for example, FIG. 15A). The collar 1026 may be supported by one or more supports, such as support 1027, which may extend from the collar to the circumference of the jig. The supplemental guide post may be positioned according to the installation position of the acetabular cup. The second patient-specific jig 1000 includes a height h2, which is selected so that, if the reference end 1020 contacts a reamed acetabulum, or if at least one of the alignment members 1005a, 1005b, 1005c is not in contact with a respective selected area of the coxal bone, the surgeon will know that additional reaming is necessary before installing the supplemental guide post and placing the final acetabular prosthesis. This is discussed further below. Understandably, height h2 can be greater than height h1, in part because bone is reamed between usage of the first and second jigs.

The reaming process may cause undercuts to develop in the acetabulum. An undercut occurs when the reamer removes material from the interior of the acetabulum and cuts underneath other areas of the coxal, for example, beneath the acetabular margin. If a jig is created to fit against the entire reamed surface of the acetabulum, it would not fit. Therefore, the second patient-specific jig 1000, and other jigs, in particular jigs for use after reaming, may include a cutout 1030 that does not closely match the surface of the reamed acetabulum, permitting easy installation and removal of the jig from an acetabulum and, in particular, a reamed acetabulum.

Figure 25C:
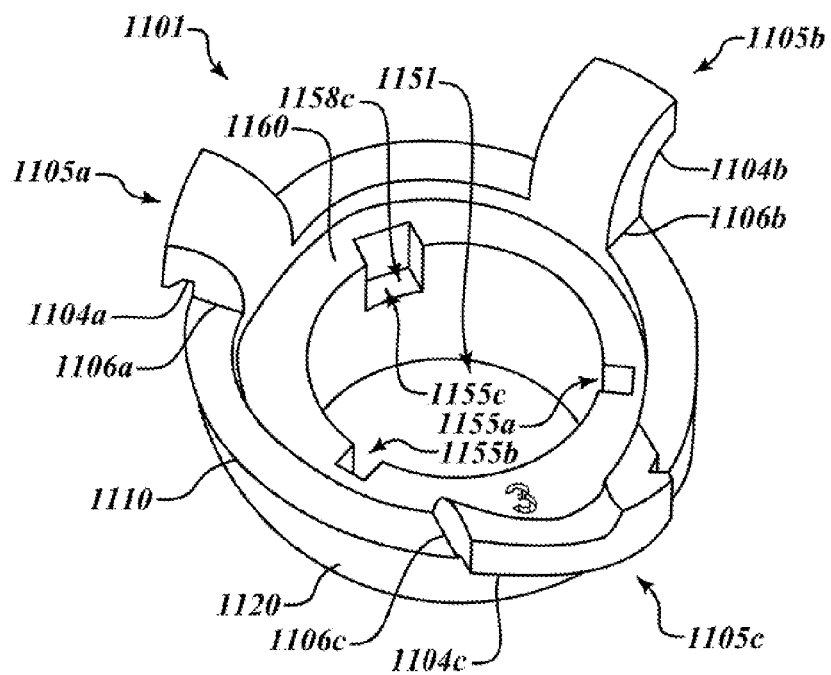
FIG. 25C is a perspective view of an outer component of the patient specific jig of FIG. 25A

FIG. 25A shows an isometric view of a third patient-specific jig assembly 1100 and FIG. 25B shows a cross-sectional view thereof. The third patient-specific jig 1100 includes two components: an outer component 1101 and an inner component 1102. The outer component 1101 of the third patient-specific jig 1100 includes three alignment members 1105a, 1105b, 1105c that extend from a circumference end 1110 of the third patient-specific jig 1100 at positions selected to contact certain areas of the coxal bone (see, for example, FIG. 9A (generically) and FIG. 17B (specifically)). As best shown in FIG. 25C, the alignment members 1105a, 1105b, 1105c are attached to the third patient-specific jig 1100 at respective attachment portions 1106a, 1106b, 1106c, similar to the first patient-specific jig 900. The angle and position of each alignment member 1105a, 1105b, 1105c relative to the circumference end 1110 is determined according to the particular position and surface of the selected areas of the coxal bone of the patient that the alignment members 1105a, 1105b, 1105c are designed to contact during the operation. The angle and position of each alignment member 1105a, 1105b, 1105c may be the same or different than that of the alignment members of the first and second patient-specific jigs of FIGS. 23A and 24A. Each alignment member 1105a, 1105b, 1105c includes an engagement portion 1104a, 1104b, 1104c, respectively, that contacts respective selected areas of the coxal bone. For example, see FIGS. 17A and 17B for illustrations of the position of alignment members relative to a third patient-specific jig and selected areas of a patient's coxal bone.

Figure 25D:
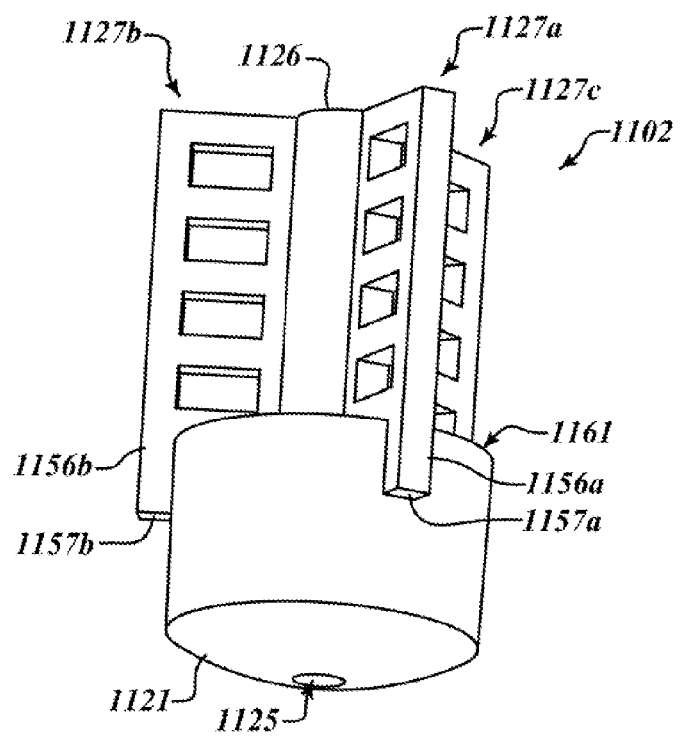
FIG. 25D is a perspective view of an inner component of the patient specific jig of FIG. 25A

FIG. 25C shown the outer component 1101 and FIG. 25D shows the inner component 1102. The outer component 1101 of the third patient-specific jig 1100 includes an aperture 1151 that accepts the inner component 1102. The aperture 1151 includes at least one, and preferably three, alignment structures or keyways 1155a, 1155b, 1155c. Each alignment keyway 1155a, 1155b, 1155c may be sized and shaped to accept one of the alignment structures or keys 1156a, 1156b, 1156c of the interior component 1102 and can be configured to only allow the interior component 1102 to fit within the aperture 1151 in a single orientation. The depth of the keyways 1155a, 1155b, 1155c and length of the alignment keys 1156a, 1156b, 1156c can be sized such that when the inner component is properly fit to the outer component, the bottom surface 1157a, 1157b, (1157c, FIG. 25B) (see FIG. 25D) of each alignment key 1156a, 1156b, (1156c, not shown) contacts the shelf (1158a, 1158b, not shown), 1158c (see FIG. 25C) of a respective keyway. The illustrated keyways and alignment keys are also sized and shaped such that when the inner component is properly fit to the outer component, the inner component alignment surface 1161 is flush or co-planar with the outer component alignment surface 1160. These features provide the surgeon with an easy way to determine if the reaming is complete and that the two jig components properly fit in the joint and with each other.

In some embodiments, the alignment structures or keyways of an outer component may be disposed along the circumference of an aperture of the outer component, as shown in FIG. 25A. In some embodiments the alignment structures may be at other locations on the outer component, for example, displaced a distance from the circumference of the aperture of the outer component.

In some embodiments, the alignment structures or keys of an inner component may be disposed along the circumference of the inner component, as shown in FIG. 25B. In some embodiments the alignment structures may be at other locations on the inner component, for example, displaced a distance from the circumference of the inner component.

The third patient-specific jig 1100 includes an aperture 1125 that extends from a reference end 1121 to a distal end of the of the first patient-specific jig 1100. The aperture 1125 is sized and configured to receive the supplemental guide post positioned in a patient (see, for example, FIG. 17A). The collar 1126 may be supported by one or more supports 1127a, 1127b, 1127c which may extend from the collar to an alignment surface 1161 of the jig. In addition to supporting the collar 1126, the supports 1127a, 1127b, 1127c also provide a place for a surgeon to grip and handle the interior component 1102. As further described below, the supplemental guide post is positioned according to an installation position of the acetabular component.

The two-component design of the third patient-specific jig 1100 provides for easy placement and removal of the jig in a reamed acetabulum. In placing the jig, a surgeon may first align and place the outer component 1101 of the third patient-specific jig 1100 in the reamed acetabulum. The surgeon may then verify that the reference end 1120 of the outer component does not contact the reamed acetabulum. Then, the surgeon may place the inner component 1102 into the aperture 1151 of the outer component 1101 while aligning the alignment keys 1156a, 1156b, 1156c with the keyways 1155a, 1155b, 1155c. The surgeon may then check that the inner component alignment surface 1161 is co-planar with the outer component alignment surface 1160. If they are co-planar, the reaming is complete. If they are not co-planar, for example, when the reference end 1121 of the inner component 1102 contacts a portion of the acetabulum, the surgeon may need to conduct additional reaming.

In addition, the third patient-specific jig 1100 includes a height h3, which is selected so that the surgeon will know if additional reaming is necessary before installing the acetabular component in the patient. The surgeon may know more reaming is necessary if the reference ends 1120, 1121 contact a reamed acetabulum, and at least one of the alignment members 1105a, 1105b, 1105c is not in contact with a respective selected area of the coxal bone, or if the alignment surfaces 1160 and 1161 are not co-planar. Understandably, height h3 can be greater than height h2 because bone may be reamed between usage of the second and third jigs, and because the second patient-specific jig may be used for purposes of positioning the supplemental guide post, while the third patient-specific jig may be used for purposes of determining whether additional reaming is necessary before installing the acetabular component in the patient.

Once the third patient-specific jig is in place and no more reaming is required, the surgeon may install a supplemental guide post through the aperture 1125 and into the patient.

With the guide post in place, the surgeon may remove the third patient-specific jig 1100. If the third patient specific jig 1100 is a single component, the surgeon, in removing the jig, may push against the guide post, knocking the jig out of position or out of the patient altogether. With the two-component jig, the surgeon may remove the inner component 1102 by sliding it along the guide post and out of the acetabulum. The aperture 1151 of the outer component may be aligned with and/or concentric with the guide post. In some embodiments, the central axis of the aperture 1151 may coincide with or be parallel to the central axis of the guide post. In still other embodiments, the aperture 1151 and inner component 1102 may be configured such that inner component 1102 is removed in a direction substantially parallel to the central axis of the guide post. With the inner component 1102 removed, the surgeon now has ample room to remove the outer component 1101 with much less risk of altering the position of the guide post.

The physician may then place an implant or prosthesis over the guide post and into the acetabulum, and then use a cannulated impactor to place the prosthetic into the jip joint.

In some embodiments, a surgeon may only use a single jig when replacing a joint. For example, a surgeon may use conventional joint replacement techniques for the bone material removal or reaming process and then use a single patient-specific jig to confirm adequate removal of material. In some embodiments, a surgeon may use a single jig to confirm adequate removal of bone material and to guide the placement of the final prosthetic, for example, by guiding the installation of a guide post. Bone or other anatomic structures may be removed with reamers, burrs, rongeurs, drills or any other instrument.

26A and 26B show an embodiment of a cannulated impactor assembly. FIG. 26A shows a side view of the cannulated impactor assembly 1200. FIG. 26B shows a cross-sectional view of the cannulated impactor assembly 1200. The cannulated impactor assembly 1200 includes a cannulated impactor 1210. The cannulated impactor is comprised of a shaft 1211 that joins an anvil 1213 at a first end of the shaft 1211 with a second end 1212 configured to accept a head 1220. The second end may be a tapered, as shown in FIGS. 26A and 26B.

The tapered end facilitates alignment of the head 1220 with the cannulated impactor 1210.

As shown in FIG. 26B, the impactor 1210 includes a cannulated channel or cavity 1214. The cannulated channel 1214 receives a guide post 1270 for guiding the placement of an acetabular component. The cannulated channel 1214 may also receive a sheath 1230. The sheath 1230 may fit within the cannulated channel 1214 and around the guide post 1270. The sheath 1230, guide post 1270, and cannulated channel 1214 may slidingly engage with each other. In some embodiments the respective diameters of a sheath, guide post, and cannulated channel allow for 0.1 mm clearance between the inner diameter of an outer part and the outer diameter of an inner part. In some embodiments, the cannulated channel may be blind, for example, as illustrated in FIG. 26B.

The head 1220 may include an aperture 1222 configured to slidably engage with the sheath 1230 and/or the guide post 1270. The head 1220 may include an engagement surface, such as the illustrated engagement surface 1221, which is configured to engage with an end of a cannulated impactor. In the illustrated embodiment, the head 1220 has a tapered engagement surface 1221 configured to engage with the tapered second end 1212 of the shaft 1211.

In some embodiments, the second end 1212 and engagement surface 1221 may each include complementary threads. In such an embodiment, the second end 1212 screws into the engagement surface 1221.

The guide post 1270 may include a bone engagement end 1271. The bone engagement end my include threads for engaging the bone and retaining the guide post 1270 in a patient's bone. In some embodiments, for example, the embodiment shown in FIGS. 26A and 26B, the engagement end 1271 may have a tapered point to engage the patient's bone.

It will be appreciated that each or all of the alignment members of any one of the patient-specific jigs disclosed herein may be formed in various configurations and shapes. For example, an alignment member may be an arc shaped or other non-linear shaped member, or it may have two or more angled surfaces. The alignment members and engagement portions may be parts of a continuous rim or lip that extends out from the entirety of the circumference end of a jig. The exact shape, position, and alignment of each alignment member may be determined by the surgeon and the computing system during preoperative planning depending upon the specific bone structure of the patient and the installation position of the acetabulum component. Any three points adjacent to a joint, such as an acetabulum, may be used as a reference location to determine and place a jig, a joint replacement, or an acetabulum implant in a desired position.

In some embodiments, a patient-specific jig may include one or more alignment members. In some embodiments, one or more alignment members may extend from the circumference of the jig and be contoured or shaped such that each alignment member may include one, two, three, or more engagement portions each contoured or shaped to match up with a respective one, two, three, or more selected areas near the joint, for example the coxal bone.

In some embodiments, a single alignment member may extend around substantially the entire circumference of the patient-specific jig. In doing so, the single alignment member may include one, two, three, or more engagement portions that are contoured or shaped to match up with an area near the joint.

In some embodiments, a single alignment member may extend around more than 180 degrees of the circumference of the patient-specific jig. In some embodiments, an alignment member may extend around less than 180 degrees, 120-180 degrees, or 240-360 degrees of the circumference of the patient-specific jig.

In some embodiments, a single alignment member may extend around the circumference of a patient specific jig such that two or more engagement portions of the single alignment member are contoured or shaped to match up with respective areas near the joint.

In some embodiments, two alignment members may extend from the circumference of a patient-specific jig. A first alignment member may include two or more engagement portions that are contoured or shaped to match up with a respective area near the joint. A second alignment member may include one or more engagement portions that are contoured or shaped to match up with a respective area near the joint. In a preferred embodiment the first and second alignment members may extend from opposing sides of the circumference of a patient specific jig.

It will also be appreciated that although the jigs, impactors, and methods have been descried in reference to a human hip joint, they are not limited to those applications. The jigs, impactors, and methods are also applicable to other joints, such as a shoulder joint, and to animals other than humans, such as horses, dogs, apes, etc.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for use in joint replacement surgery, the device comprising:

a patient-specific jig having a body formed using medical imaging data corresponding to an anatomic structure of a patient and a model of a reamed surface of the anatomic structure of the patient, the body having a proximal end and a distal end and being configured to be positioned against the anatomic structure of the patient at a joint location, the body comprising a first patient-specific jig component and a second patient-specific jig component, the first patient-specific jig component including an aperture for receiving the second patient-specific jig component, the first patient-specific jig component having a first alignment structure configured to align with a second alignment structure on the second patient-specific jig component when the first patient specific jig component and the second patient-specific jig component are both properly positioned with respect to the anatomic structure and each other and indicating adequate reaming of a portion of the anatomic structure of the patient, the first patient-specific jig component including a first alignment member located adjacent the proximal end of the body, the first alignment member configured to position and orient the body with respect to the anatomic structure of the patient to indicate information to a surgeon corresponding to a final installation position of a prostheses to be secured to the anatomic structure of the patient according to the medical imaging data, the second patient-specific jig component including a reference end that conforms to the depth and shape of the model of the reamed surface of the anatomic structure of the patient, the second patient-specific jig including a guide post aperture extending through the body from the reference end that matches a reamed surface of the anatomic structure of the patient to a distal end of the body, the guide post aperture aligns a guide post according to the final installation position of the prostheses.

2. The device for use in joint replacement surgery of claim 1 wherein the medical imaging data includes one or more of two-dimensional x-rays, MRI scans, or CT scan.

3. The device for use in joint replacement surgery of claim 1 wherein the medical imaging data includes a combination of two-dimensional medical image data and three-dimensional medical image data.

4. The device for use in joint replacement surgery of claim 1 wherein the second alignment structure is an alignment key and the first alignment structure is an alignment keyway, the second alignment structure is configured to engage with the first alignment structure to engage the first patient-specific jig component relative to the second patient specific jig component in a single orientation.

5. The device for use in joint replacement surgery of claim 4 wherein the first alignment structure has a first size and shape and the second alignment structure is configured with a size and shape to accept the first alignment structure, and wherein the first patient-specific jig component includes a third alignment structure configured to align and engage with a fourth alignment structure on the second patient-specific jig component when the first patient specific jig component and the second patient-specific jig component are both properly positioned with respect to the anatomic structure and each other and indicating adequate reaming of a portion of the anatomic structure of the patient, the fourth alignment structure having a second size and shape different than the first size and shape and the third alignment structure configured with a size and shape to accept the third alignment structure.

6. The device for use in joint replacement surgery of claim 1 wherein the first patient-specific jig component includes a first alignment surface and the second patient-specific jig component includes a second alignment surface, the first and second alignment surfaces indicate the information to the surgeon corresponding to the installation position of a prostheses implant to be secured to the anatomic structure of the patient.

7. The device for use in joint replacement surgery of claim 1 wherein the first alignment member is configured to position and orient the body with respect to the anatomic structure of the patient to indicate adequate removal of anatomic structure.

8. The device for use in joint replacement surgery of claim 1 wherein the patient-specific jig is configured such that the alignment of the first patient specific jig component with the second patient-specific jig component and alignment of the first alignment member with a selected point of the anatomic structure, confirms adequate removal of anatomic structure and guides placement of the prosthesis.

9. A device for use in joint replacement surgery, the device comprising:
a patient-specific jig having a body formed using medical imaging data corresponding to an anatomic structure of a patient and a model of a reamed surface of the anatomic structure of the patient, the body having a proximal end and a distal end and configured to be positioned against the anatomic structure of the patient at a joint location, the body including a first alignment member located adjacent the proximal end of the body, the first alignment member configured to position and orient the body with respect to the anatomic structure of the patient to indicate information to a surgeon corresponding to a final installation position of a prostheses to be secured to the anatomic structure of the patient according to the medical imaging data, the body including a reference end that matches a depth and extends along and matches at least a portion of the shape of the model of the reamed surface of the anatomic structure of the patient, the body including an aperture therethrough extending from the reference end to a distal end of the body, the aperture configured to align a guide post according to the final installation position of the prostheses.

10. The device for use in joint replacement surgery of claim 9 wherein the first alignment member extends around a circumference of the proximal end of the body.

11. The device for use in joint replacement surgery of claim 9 wherein the first alignment member extends less than 180 degrees around a circumference of the proximal end of the body.

12. The device for use in joint replacement surgery of claim 9 wherein the first alignment member includes three engagement portions.

13. The device for use in joint replacement surgery of claim 9, further comprising:
a second alignment member located adjacent the proximal end of the body and opposing the first alignment member.

14. The device for use in joint replacement surgery of claim 13 wherein the first alignment member includes two engagement portions and the second alignment member includes one engagement portion.

15. The device for use in joint replacement surgery of claim 9 wherein the patient is a human.

16. The device for use in joint replacement surgery of claim 9 wherein the medical imaging data includes one or more of two-dimensional x-rays, MRI scans, or CT scan.

17. The device for use in joint replacement surgery of claim 9 wherein the body is configured to guide the placement of the prostheses.

18. The device for use in joint replacement surgery of claim 9 wherein the information indicated to the surgeon corresponding to a final installation position of the prostheses includes information to indicate adequate removal of anatomic structure.

* * * * *